United States Patent [19]

Masaki et al.

[11] Patent Number: 4,596,803

[45] Date of Patent: * Jun. 24, 1986

[54] PIPERAZINE DERIVATIVES AND A MEDICINE CONTAINING THE SAME

[75] Inventors: Tomoh Masaki, Ibaragi; Toshiro Kamishiro; Takashi Okazoe, both of Misato, all of Japan; Koichi Kumakura, London, England; Mitsuo Masaki, Chiba, Japan

[73] Assignee: Nippon Chemiphar Co., Ltd., Tokyo, Japan

[*] Notice: The portion of the term of this patent subsequent to Mar. 26, 2002 has been disclaimed.

[21] Appl. No.: 587,545

[22] Filed: Mar. 8, 1984

Related U.S. Application Data

[62] Division of Ser. No. 361,506, Mar. 25, 1982, Pat. No. 4,507,297.

[30] Foreign Application Priority Data

Apr. 10, 1981 [JP] Japan .................................. 56-53116

[51] Int. Cl.[4] .................. A61K 31/505; C07D 405/14; C07D 405/12
[52] U.S. Cl. .................... 514/252; 544/295; 544/360; 544/374
[58] Field of Search .................. 544/295, 360, 374; 424/250, 251; 534/252

[56] References Cited

U.S. PATENT DOCUMENTS 2,963,482 12/1960 Cochran, Jr. et al. .............. 544/374
2,963,483 12/1960 Cochran, Jr. et al. .............. 544/374
4,032,567 6/1977 Klieger et al. ...................... 544/391

OTHER PUBLICATIONS

Morrison et al., *Organic Chemistry*, Sec. Ed., 1966, Allyn and Bacon, Inc., Boston, pp. 589–591, 603.

*Primary Examiner*—Glennon H. Hollrah
*Assistant Examiner*—James H. Turnipseed
*Attorney, Agent, or Firm*—Oblon, Fisher, Spivak, McClelland & Maier

[57] ABSTRACT

A compound is disclosed which has the formula,

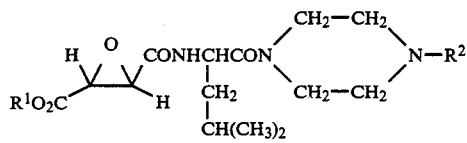

where $R^1$ is a hydrogen atom, or a straight or branched chain alkyl group having 1 to 4 carbon atoms, and $R^2$ is a straight or branched chain alkyl group having 1 to 4 carbon atoms,

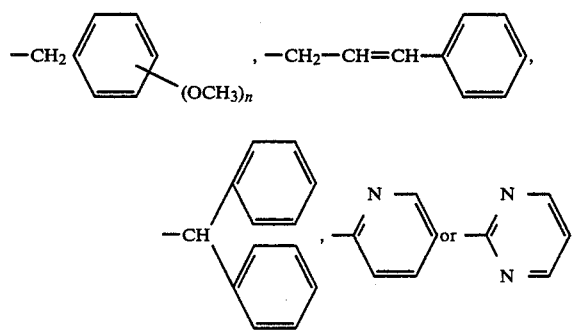

in which n is an integer of 0 to 3, or a pharmaceutically acceptable salt thereof. A process for producing the compound and a medicine containing the compound are also disclosed. Such medicine is effectively useful for inhibiting myocardial infarction.

11 Claims, No Drawings

PIPERAZINE DERIVATIVES AND A MEDICINE CONTAINING THE SAME

This is a division of application Ser. No. 361,506, filed Mar. 25, 1982, now U.S. Pat. No. 4,507,297.

BACKGROUND OF THE INVENTION

1. Field of the Invention

The present invention relates to novel piperazine derivatives. Further, the invention is concerned with a process for the production of these piperazine derivatives and medicines containing such compounds which are effective to prevent or cure myocardial infarction.

2. Description of the Prior Art

There is a tendency of myocardial infarction-bearing patients increasing as the population of the aged increases. Therefore, the medical prevention and treatment of myocardial infarction are greatly important from a viewpoint of national health protection.

However, myocardial infarction is extremely difficult to medically prevent or treat even with the modern medical science. The presently prevalent approach to the medical prevention and treatment of myocardial infarction is to administer medicines for controlling or curing cardiac insufficiency, arrhythmia or ischemic heart disease which is liable to produce myocardial infarction. This gives an impetus to the development of any medicines effective to medically prevent or treat myocardial infarction.

The present inventors have conducted continuous researches for medicines having superior medicinal activities for the prevention or cure of myocardial infarction. They have synthesized some novel compounds represented by the general formula (1) as will be described later, and as a result, have discovered that these compounds exhibit markedly superior inhibitive activities against myocardial infarction and have a high level of safety. This discovery has led to the present invention.

SUMMARY OF THE INVENTION

The present invention provides novel piperazine derivatives and pharmaceutically acceptable salts thereof.

This invention also provides a process for the production of these piperazine derivatives and pharmaceutically acceptable salts thereof.

The present invention provides as well medicines containing such compounds which are effectively useful for inhibiting myocardial infarction.

Various objects and advantages of the present invention as will hereinafter become more apparent are achieved by providing a compound of the formula (1),

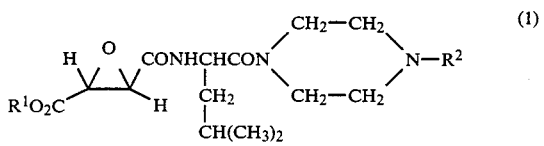

where $R^1$ is a hydrogen atom, or a straight or branched chain alkyl group having not more than 4 carbon atoms, and $R^2$ is a straight or branched chain alkyl group having not more than 4 carbon atoms,

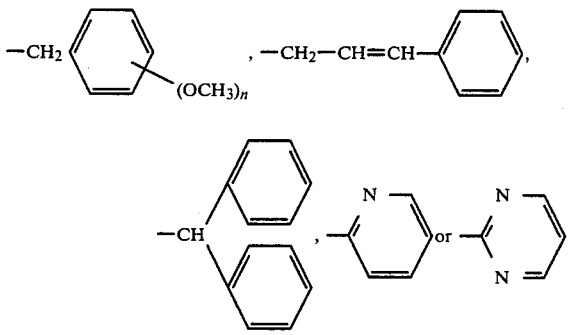

in which n is an integer of from 0 to 3, or a pharmaceutically acceptable salt thereof.

DETAILED DESCRIPTION OF THE PREFERRED EMBODIMENTS

Piperazine derivatives of the present invention are compounds represented by the following general formula (1),

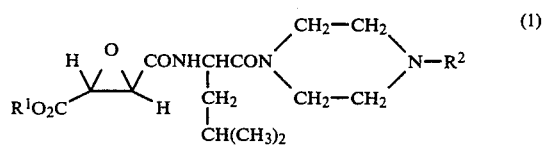

where $R^1$ is a hydrogen atom, or a straight or branched chain alkyl group having not more than 4 carbon atoms, and $R^2$:S a straight or branched chain alkyl group having not more than 4 carbon atoms,

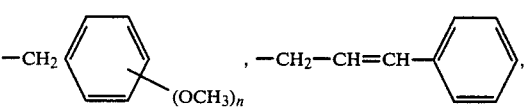

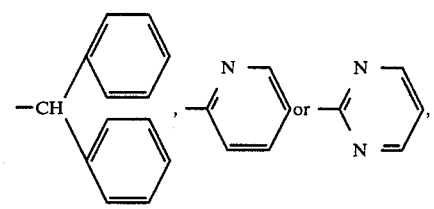

in which n is an integer of from 0 to 3, and pharmaceutically acceptable salts thereof.

Examples of the compounds represented by the formula (1) typically include trans-3-[(s)-3-methyl-1-(4-methylpiperazine-1-yl carbonyl)butyl-carbamoyl]oxirane-2-carboxylic acid, trans-3-[(s)-1-(4-ethylpiperazine-1-yl carbonyl)-3-methylbutylcarbamoyl]oxirane-2-carboxylic acid, trans-3-[(s)-1-(4-isobutylpiperazine-1-yl carbonyl)-3-methylbutyl-carbamoyl]-oxirane-2-carboxylic acid, trans-3-[(s)-1{4-(4-methoxyphenylmethyl)piperazine-1-yl carbonyl}-3-methylbutyl-carbamoyl]-oxirane-2-carboxylic acid, trans-3-[(s)-1-{4-(3,4-dimethoxyphenylmethyl)piperazine-1-yl carbonyl}3-methylbutyl-carbamoyl]-oxirane-2-carboxylic acid, trans-3-[(s)-3-methyl-1-{4-(2,3,4-trimethoxyphenylmethyl)piperazine-1-yl carbonyl}butylcarbamoyl]-oxirane-2-carboxylic acid, trans-3-[(s)-3-methyl-1-{4-(3,4,5-trimethoxyphenylmethyl)piperazine-1-yl carbonyl}butylcarbamoyl]-oxirane-2-carboxylic acid, trans-3-[(s)-1-(4-benzylpiperazine-1-yl carbonyl)-3-methylbutylcarbamoyl]oxirane-2-carboxylic acid, trans-3-[(s)-1-(4-cinnamylpiperazine-1-yl carbonyl)-3-methylbutyl-carbamoyl]oxirane-2-carboxylic acid, trans-3-[(s)-1-(4-diphenylmethylpiperazine-1-yl carbonyl)-3-methylbutylcarbamoyl]oxirane-2-carboxylic acid, trans-3-[(s)-1-{4-(2-pyridyl)piperazine-1-yl carbonyl}-3-methylbutylcarbamoyl]oxirane-2-carboxylic acid, and trans-3-[(s)-3-methyl-1-{4-(2-pyrimidinyl)piperazine-1-yl carbonyl}butylcarbamoyl]-oxirane-2-carboxylic acid.

These compounds may be suitably used for the practice of the invention, irrespective of whether their epoxy groups are optically active or inactive.

Methyl esters, ethyl esters, n-propyl esters, isopropyl esters, n-butyl esters, isobutyl esters, sec-butyl esters and tert-butyl esters of the above-mentioned compounds are also encompassed by the invention.

According to another aspect of the invention, there is provided a process for the production of the compounds represented by the formula (1). The process is carried out as follows:

In the case where $R^1$ in the formula (1) is an alkyl group, a leucine derivative represented by the general formula (2),

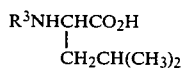
(2)

where $R^3$ is a protective group for an amino group of an amino acid such as a tert-butoxycarbonyl group, or its reactive derivative, is reacted with an amino derivative represented by the general formula (3),

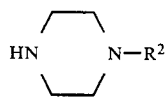
(3)

where $R^2$ is the same as defined above, to obtain a compound represented by the general formula (4),

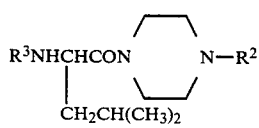
(4)

where $R^2$ and $R^3$ are the same as defined above. Subsequently, the protective group is removed by any conventional method, and a leucylpiperazine derivative thus obtained and represented by the general formula (5),

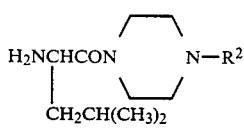
(5)

where $R^2$ is the same as defined above, is reacted with a trans-epoxy succinic acid monoester represented by the general formula (6),

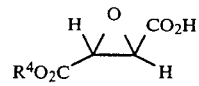
(6)

where $R^4$ is a straight or branched chain alkyl group having not more than 4 carbon atoms, or its reactive derivative, thereby obtaining a compound represented by the general formula (7),

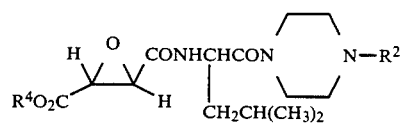
(7)

where $R^2$ and $R^4$ are the same as defined above.

Alternatively, the trans-epoxy succinic acid monoester of the formula (6) above or its reactive derivative is reacted with leucine to obtain an epoxy succinyl leucine derivative represented by the general formula (8),

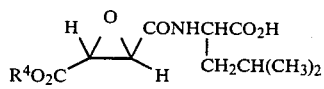
(8)

where $R^4$ is the same as defined above, or its reactive derivative. The compound of the formula (8) is then reacted with an amine derivative represented by the formula (3) above, thereby obtaining a compound of the formula (7) above.

The condensation reaction of the compound of the formula (2) with the compound of the formula (3), the condensation reaction of the formula (5) with the compound of the formula (6) and the condensation reaction of the compound of the formula (8) with the compound of the formula (3) are conducted by a usual acid halide method or a mixed anhydride method, or in an organic solvent such as methylene chloride, ethylene chloride, chloroform, ethyl acetate, tetrahydrofuran or the like in the presence of a known condensation agent such as N-hydroxy succinimide and N,N'-dicyclohexylcarbodimide at $-10°$ to $+40°$ C., preferably at $-5°$ to $+30°$ C.

The ester residue of the compound represented by the formula (7) can be readily converted to the corresponding carboxylic acid by any existing alkaline hydrolysis method.

A compound represented by the general formula (9),

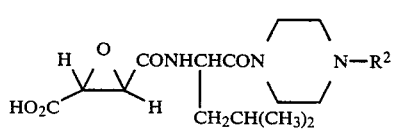
(9)

where $R^2$ is the same as defined above, which corresponds to the compound of the formula (1) where $R^1$ is a hydrogen atom, can be obtained by hydrolyzing the ester group of the compound of the formula (7).

The piperazine derivative thus prepared may be optionally converted to a pharmaceutically acceptable salt thereof, for example, of sodium, potassium, calcium or magnesium, or trialkylamine, dibenzylamine, N-lower alkylpiperidine, N-benzyl-β-phenetylamine, α-phenethylamine, 1-(1-naphthyl)ethylamine as well as hydrochloric acid, hydrobromic acid, formic acid, sulfuric acid, fumaric acid, maleic acid or tartaric acid. Further, with use of an optically active trans-epoxy succinic acid monoester (6) such as a (2S,3S)-epoxy succinic acid monoester or a (2R,3R)-epoxysuccinic acid monoester which may be synthesized in accordance with the method of Kenji Mori et al [Tetrahedron, vol. 36(1), 87 to 90 (1980)], it is possible to obtain a compound (1) of the present invention, which has an optically active epoxy succinic acid group, by the process noted above.

According to a further aspect of the invention, there are provided medicines for preventing or curing myocardial infarction, which contain the compounds of the formula (1) or their pharmaceutically acceptable salts as active ingredients.

The usefulness of the compounds of the formula (1) and their pharmaceutically acceptable salts according to the present invention as medicines for myocardial infarction has been confirmed by the fact that they have superior preventive and curative effects against an experimental myocardial infarction model. Namely, when administered in an amount of from 1 to 400 mg/kg against an experimental myocardial infarction of a rabbit or a dog, these compounds exhibited remarkably preventive and curative effects. For instance, substantial suppression of myocardial infarction by such compounds was observed when a 40 to 200 mg/kg amount was administered to rabbits.

Moreover, from the acute toxicity tests using mice, the compounds of the invention were found to be quite safe to human bodies.

The dosage of the compounds of the formula (1) and their pharmaceutically acceptable salts varies depending upon the degrees of myocardial infarction symptoms. Generally, they may be administered to patients in an amount of from about 100 mg to about 1 g.

For various formulations as medicines for myocardial infarction, the compounds of the formula (1) and their salts may usually be combined with pharmaceutical carriers to prepare pharmaceutical compositions. Examples of the carriers include diluents or vehicles such as a filler, a binding agent, a disintegrator and a lubricant.

Such medicines are available in the dosage form of an injection, a powder, a capsule, a granule, a tablet or an ampoule.

In the case of a tablet, a carrier is used which may be selected, for example, from a vehicle such as lactose, saccharose, sodium chloride, a glucose solution, starch, calcium carbonate, crystal cellulose or silicic acid; a binder such as water, ethanol, propanol, glucose, a starch solution, a gelatin solution, carboxylmethyl cellulose, methyl cellulose or potassium phosphate; a disintegrator such as dried starch, sodium alginate, an agar powder, sodium hydrogencarbonate, calcium carbonate, stearic acid monoglyceride, starch or lactose; or a lubricant such as a stearate, a boric acid powder or solid polyethylene glycol which is known in the art. Where it becomes desirable, the tablet may be sugar- or gelatin-coated, or film-coated.

In the case of an injection, a diluent is used which may be selected, for example, from water, ethyl alcohol, propylene glycol, polyoxyethylene sorbit or a sorbitan ester. In such instance, sodium chloride, glucose or glycerine may be added in an amount sufficient to form an isotonic solution. A commonly used dissolving assistant, a buffer, a pain reliever or a preserving agent may also be conveniently incorporated.

This invention will be described in more detail with reference to certain specific examples and test examples which are provided for purposes of illustration only and are not construed as limiting. The test examples are intended to show the compounds of the formula (I) and their pharmaceutically acceptable salts as exhibiting superior preventive or curative effects against myocardial infarction models and having a high level of safety.

EXAMPLES

Example 1

To a methylene chloride solution (100 ml) containing tert-butoxycarbonyl-L-leucine monohydrate (9.96 g) and N-hydroxy succinimide (4.6 g) was added dropwise a methylene chloride solution (50 ml) of N,N'-dicyclohexylcarbodiimide (8.24 g) with a length of time for 1 hour under cooling with ice. After being stirred at room temperature for 4 hours, the reaction mixture was again cooled with ice, and a methylene chloride solution (50 ml) of 1-(diphenylmethyl)piperazine (10.08 g) was added dropwise in 20 minutes. The mixture was stirred overnight at room temperature. Following the removal of the precipitate by filtration, the solvent was removed by distillation under reduced pressure, and ethyl acetate was added. After any insoluble matters were again removed by filtration, the filtrate was washed first with an aqueous sodium bicarbonate solution and then with a saturated sodium chloride solution, dried over magnesium sulfate and distilled under reduced pressure to remove the solvent, whereupon a crude reaction mixture was obtained. This reaction mixture was purified by silica gel column chromatography (developing solvent: chloroform followed by chloroform:methanol=50:1) to yield 16.5 g of tert-butyl (s)-1-(4-diphenylmethylpiperazine-1-yl carbonyl)-3-methylbutylcarbamate as a colorless amorphous substance (yield: 89%).

| NMR (CDCl$_3$)δ: | |
|---|---|
| 0.86 | (3H, d, (CH$_3$)$_2$CH—) |
| 0.92 | (3H, d, (CH$_3$)$_2$CH—) |
| 1.38 | (9H, s, (CH$_3$)$_3$C—) |
| 1.3–1.9 | (3H, m, —CH$_2$—CH—) |
| 2.3 | (4H, m, —CON(CH$_2$CH$_2$)$_2$N—) |
| 3.5 | (4H, m, —CON(CH$_2$CH$_2$)$_2$N—) |

| NMR (CDCl$_3$)δ: | |
|---|---|
| 4.12 | (1H, s, —C<u>H</u>Ar$_2$) |
| 4.48 | (1H, m, —NH—C<u>H</u>—CO—) |
| 5.18 | (1H, br, —NH) |
| 7.0–7.3 | (10H, m, aromatic protons) |

Under cooling with ice, hydrogen chloride gas was fed and saturated into ethyl acetate (300 ml), and an ethyl acetate solution (80 ml) of tert-butyl (s)-1-(4-diphenylmethylpiperazine-1-yl carbonyl)-3-methylbutyl carbamate (16.5 g) obtained above was added dropwise in 10 minutes. After stirring at room temperature for 2 hours, the solvent and residual hydrogen chloride were continuously removed by distillation under reduced pressure to yield 15.6 g of 4-diphenylmethyl-1-L-leucylpiperazinedihydrochloride as a light yellow crystal (yield: quantitative).

Under cooling with ice, a methylene chloride solution (50 ml) of N,N'-dicyclohexylcarbodiimide (7.31 g) was added dropwise in 1 hour to a methylene chloride solution (100 ml) containing monoethyl trans-epoxy succinate (5.68 g) and N-hydroxysuccinimide (4.08 g). After being stirred at room temperature for 4 hours, the mixture was again cooled with ice to which was then added 4-diphenylmethyl-1-L-leucylpiperazinedihydrochloride (15.6 g) obtained above. Thereafter, triethylamine (7.9 g) was added dropwise in 5 minutes, and the mixture was stirred overnight at room temperature. Following the removal of the solvent by distillation under reduced pressure, ethyl acetate (250 ml) was added to the residue. After any insoluble matters were removed by filtration, the filtrate was washed first with an aqueous sodium bicarbonate solution and then with an aqueous saturated sodium chloride solution, dried over magnesium sulfate and distilled under reduced pressure to remove the solvent, whereupon a crude reaction mixture was obtained. This reaction mixture was purified by silica gel column chromatography (developing solvent: chloroform followed by chloroform:methanol=50:1) to yield 13.3 g of ethyl trans-3-[(s)-1-(4-diphenylmethylpiperazine-1-yl carbonyl)-3-methylbutyl carbamoyl]oxirane-2-carboxylate as a light yellow amorphous substance (yield: 74%).

IR(KBr)cm$^{-1}$: 1750, 1630, 890.

| NMR (CDCl$_3$)δ: | |
|---|---|
| 0.90 | (3H, d, (CH$_3$)$_2$CH—) |
| 0.94 | (3H, d, (CH$_3$)$_2$CH—) |
| 1.26 | (3H, t, J = 7Hz, —CO$_2$CH$_2$C<u>H</u>$_3$) |
| 1.4–1.8 | (3H, m, —C<u>H</u>$_2$—C<u>H</u>—) |
| 2.4 | (4H, m, —CON(CH$_2$CH$_2$)$_2$N—) |
| 3.6–3.8 | (6H, m, —CON(CH$_2$CH$_2$)$_2$N—, —C<u>H</u>—O—C<u>H</u>) |
| 4.30 | (2H, q, J = 7Hz, —CO$_2$C<u>H</u>$_2$—CH) |
| 4.34 | (1H, s, —C<u>H</u>Ar$_2$) |
| 5.08 | (1H, m, —NH—C<u>H</u>—CO—) |
| 7.2–7.8 | (11H, m, Ar—H, N<u>H</u>—) |

Under cooling with ice, a 0.48N sodium hydroxide-ethanol solution (54.2 ml) was added dropwise to an ethanol solution (70 ml) of ethyl trans-3-[(s)-1-(4-diphenylmethylpiperazine-1-yl carbonyl)-3-methylbutyl carbamoyl]oxirane-2-carboxylate (13.2 g) obtained above. After stirring at room temperature for 3 hours, the solvent was removed by distillation under reduced pressure, and the reaction mixture was further dried under reduced pressure to yield 12.4 g of sodium trans-3-[(s)-1-(4-diphenylmethylpiperazine-1-yl carbonyl)-3-methylbutylcarbamoyl]oxirane-2-carboxylate as a light yellow powder (yield: 95%).

IR(KBr)cm$^{-1}$: 1630, 900.

| NMR (CD$_3$OD)δ: | |
|---|---|
| 0.92 | (6H, d, (CH$_3$)$_2$CH—) |
| 1.4–1.7 | (3H, m, —C<u>H</u>$_2$—C<u>H</u>—) |
| 2.4 | (4H, m, —CON(CH$_2$CH$_2$)$_2$N—) |
| 3.4–3.7 | (6H, m, —CON(CH$_2$CH$_2$)$_2$N—, —C<u>H</u>—O—C<u>H</u>) |
| 4.30 | (1H, s, —C<u>H</u>Ar$_2$) |
| 5.0 | (1H, m, —NH—C<u>H</u>—CO—) |
| 7.2–7.6 | (10H, m, aromatic protons) |

The thus obtained sodium salt was added to an equivalent amount of 0.1N hydrochloric acid and left to stand. The white crystal which had precipitated was collected by filtration, washed with cold water and dried under reduced pressure to yield the corresponding free acid.

mp: 129°–132° C. (decomposed).
IR(KBr) cm⁻¹: 1640, 890.

| NMR (CD₃OD)δ: | |
|---|---|
| 0.90 | (6H, d, —CH(C$\underline{H}$₃)₂) |
| 1.4–1.7 | (3H, m, —C$\underline{H}$₂C$\underline{H}$(CH₃)₂) |
| 2.5 | (4H, m, —CON⟨CH₂—C$\underline{H}$₂ / C$\underline{H}$₂—CH₂⟩N—) |
| 3.3–3.8 | (6H, m, —CON⟨C$\underline{H}$₂—CH₂ / CH₂—C$\underline{H}$₂⟩N—, —C$\underline{H}$—O—C$\underline{H}$ ) |
| 4.36 | (1H, s, —C$\underline{H}$(C₆H₅)₂) |
| 4.8 | (1H, m, ⟩N—C$\underline{H}$—CO—) |
| 7.1–7.3 | (10H, m, —CH(C₆$\underline{H}$₅)₂) |

MS(m/e): 480(M⁺+1), 479(M⁺), 167(100%).

Elemental analysis as C₂₇H₃₃N₃O₅:
Calculated (%): C:67.62, H:6.94, N:8.76. Measured (%): C:67.45, H:7.05, N:8.55.

EXAMPLE 2

Tert-butoxycarbonyl-L-leucine monohydrate (8.92 g) and 1-benzylpiperazine (6.30 g) were condensed in the same manner as in the preparation of tert-butyl (s)-1-(4-diphenylmethylpiperazine-1-yl carbonyl)-3-methyl butylcarbamate to yield 8.06 g of tert-butyl (s)-1-(4-benzylpiperazine-1-yl carbonyl)-3-methylbutylcarbamate as a colorless amorphous substance (yield: 58%).

| NMR (CDCl₃)δ: | |
|---|---|
| 0.92 | (6H, m, (CH₃)₂C$\underline{H}$—) |
| 1.1–1.9 | (12H, m, (C$\underline{H}$₃)₃C—, —C$\underline{H}$₂—C$\underline{H}$—) |
| 2.28–2.52 | (4H, m, —CON⟨CH₂—C$\underline{H}$₂ / C$\underline{H}$₂—CH₂⟩N—) |
| 3.30–3.72 | (6H, m, —C$\underline{H}$₂Ar, —CON⟨C$\underline{H}$₂—CH₂ / CH₂—C$\underline{H}$₂⟩N—) |
| 4.52 | (1H, m, —NH—C$\underline{H}$—CO—) |
| 5.20 | (1H, m, —N$\underline{H}$) |

| NMR (CDCl₃)δ: | |
|---|---|
| 7.20 | (5H, s, aromatic proton) |

In the same manner as employed for the preparation of 4-diphenylmethyl-1-L-leucylpiperazine=dihydrochloride, 10.7 g of 4-benzyl-1-L-leucylpiperazine=-dihydrochloride was yielded as a light yellow powder (yield: 94%) from tertbutyl (s)-1-(4-benzylpiperazine-1-yl carbonyl)-3-methylbutylcarbamate (12.3 g) obtained above.

A small portion of the product was treated with two equivalents of triethylamine to obtain the corresponding free base which was found to be 4-benzyl-1-L-leucylpiperazine by NMR.

| NMR (CDCl₃)δ: | |
|---|---|
| 0.94 | (6H, d, J = 7Hz, (CH₃)₂CH—) |
| 1.36 | (2H, m, —C$\underline{H}$₂—CH—) |
| 1.90 | (1H, m, —CH₂—C$\underline{H}$—) |
| 2.16–2.68 | (6H, m, —N$\underline{H}$₂, —CON⟨CH₂—C$\underline{H}$₂ / C$\underline{H}$₂—CH₂⟩N—) |
| 3.40–4.00 | (7H, m, —CON⟨C$\underline{H}$₂—CH₂ / CH₂—C$\underline{H}$₂⟩N—, —C$\underline{H}$₂Ar, —NH—C$\underline{H}$—CO—) |
| 7.44 | (5H, s, aromatic proton) |

Monoethyl trans-epoxy succinate (4.03 g) and 4-benzyl-1-L-leucylpiperazine-dihydrochloride (9.12 g) obtained above were condensed in the same manner as employed in the preparation of ethyl trans-3-[(s)-1-(4-diphenylmethylpiperazine-1-yl carbonyl)-3-methyl-butylcarbamoyl]oxirane-3-carboxylate to yield 6.89 g of ethyl trans-3-[(s)-1-(4-benzylpiperazine-1-yl carbonyl)-3-methylbutylcarbamoyl]oxirane-2-carboxylate as a light yellow amorphous substance (yield: 63%).

IR(neat)cm⁻: 1755, 1690, 1640, 900.

| NMR (CDCl₃)δ: | |
|---|---|
| 0.92 | (6H, m, (CH₃)₂C$\underline{H}$—) |
| 1.1–1.7 | (6H, m, —C$\underline{H}$₂—C$\underline{H}$—, CO₂CH₂C$\underline{H}$₃) |
| 2.38 | (4H, m, —CON⟨CH₂—C$\underline{H}$₂ / C$\underline{H}$₂—CH₂⟩N—) |

-continued

| NMR (CDCl₃)δ: | |
|---|---|
| 3.3–3.7 | (8H, m, —CON<CH₂—CH₂\CH₂—CH₂>N—, —C$\underline{H}_2$Ar, 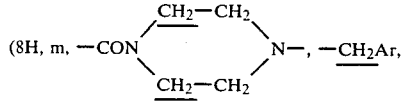 —C$\underline{H}$——C$\underline{H}$ ) |
| 4.15 | (2H, d, J = 7Hz, —CO₂C$\underline{H}_2$CH₃) |
| 4.82 | (1H, m, —NH—C$\underline{H}$—CO—) |
| 6.5–6.9 | (1H, m, —N$\underline{H}$) |
| 7.12 | (5H, s, aromatic proton) |

In the same manner as employed in the preparation of sodium trans-3-[(s)-1-(4-diphenylmethylpiperazine-1-yl carbonyl)-3-methylbutylcarbamoyl]oxirane-2-carboxylate, 6.25 g of sodium trans-3-[(s)-1-(4-benzylpiperazine-1-yl carbonyl)-3-methylbutylcarbamoyl]oxirane-2-carboxylate was yielded as a light yellow powder (yield: 99%) from ethyl trans-3-[(s)-1-(4-benzylpiperazine-1-yl carbonyl)-3-methylbutylcarbamoyl]oxirane-2-carboxylate (6.38 g) obtained above.

IR(KBr)cm⁻¹: 1615, 890.

| NMR (CD₃CD)δ: | |
|---|---|
| 0.92 | (6H, m, (C$\underline{H}_3$)₂CH—) |
| 1.3–1.75 | (3H, m, —C$\underline{H}_2$—C$\underline{H}$—) |
| 2.42 | (4H, m, —CON<CH₂—CH₂\CH₂—CH₂>N—) |
| 3.3–3.8 | (8H, m, —CON<CH₂—CH₂\CH₂—CH₂>N—, —C$\underline{H}$——C$\underline{H}$, —C$\underline{H}_2$Ar) |
| 4.85 | (1H, m, —NH—C$\underline{H}$—CO—) |
| 7.24 | (5H, s, aromatic proton) |

EXAMPLE 3

Tert-butoxycarbonyl-L-leucine monohydrate (7.47 g) and 1-(4-methoxy-phenylmethyl)piperazine (6.18 g) were condensed in the same manner as employed in the preparation of tert-butyl (s)-1-(4-diphenylmethylpiperazine-1-yl carbonyl)-3-methylbutylcarbamate to yield 12.0 g of tert-butyl (s)-1-[4-(4-methoxyphenylmethyl)-piperazine-1-yl carbonyl]-3-methylbutylcarbamate as a colorless amorphous substance (yield: 95%).

In the same manner as employed in the preparation of 4-diphenylmethyl-1-L-leucylpiperazine=dihydrochloride, 11.2 g of 1-L-leucyl-4-(4-methoxyphenylmethyl)-piperazine=dihydrochloride was yielded as a white crystal (yield: quantitative) from tert-butyl (s)-1-[4-(4-methoxyphenylmethyl)piperazine-1-yl carbonyl]-3-methylbutylcarbamate (12.0 g) obtained above.

Monoethyl trans-epoxy succinate (4.8 g) and 1-L-leucyl-4-(4-methoxyphenylmethyl)piperazine=dihydrochloride (11.2 g) obtained above were condensed in the same manner as employed in the preparation of ethyl trans-3-[(s)-1-(4-diphenylmethylpiperazine-1-yl carbonyl)-3-methylbutylcarbamoyl]oxirane-2-carboxylate to yield 5.0 g of ethyl trans-3-[(s)-1-{4-(4-methoxyphenylmethyl)piperazine-1-yl carbonyl}-3-methylbutylcarbamoyl]oxirane-2-carboxylate as a colorless amorphous substance (yield: 38%).

IR(KBr)cm⁻¹: 1750, 1630, 900.

| NBR(CDCl₃)δ: | |
|---|---|
| 0.94 | (3H, d, CH₃\CH₃>CH—) |
| 1.00 | (3H, d, CH₃\CH₃>CH—) |
| 1.32 | (3H, t, J=7Hz, —CO₂CH₃C$\underline{H}_3$) |
| 1.4–1.7 | (3H, m, —C$\underline{H}_2$—C$\underline{H}$—) |
| 2.48 | (4H, m, —CON<CH₂—CH₂\CH₂—CH₂>N—) |
| 3.5–3.8 | (8H, m, —CON<CH₂—CH₂\CH₂—CH₂>NC$\underline{H}_2$—, —C$\underline{H}$——C$\underline{H}$ ) |
| 3.92 | (3H, s, —OC$\underline{H}_3$) |
| 4.38 | (2H, d, J=7Hz, —CO₂C$\underline{H}_2$—) |
| 5.10 | (1H, m, —NH—C$\underline{H}$—CO—) |
| 7.08 | (2H, d, 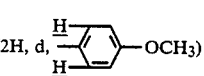) |
| 7.46 | (2H, d, 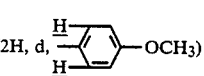) |

| NBR(CDCl₃)δ: |
|---|
| 7.0-7.4 (1H, d, —N<u>H</u>) |

MS(m/e): 461(M+), 318, 121 (100%).

In the same manner as employed in the preparation of sodium trans-3-[(s)-1-(4-diphenylmethylpiperazine-1-yl carbonyl)-3-methylbutylcarbamoyl]oxirane-2-carboxylate, 4.8 g of sodium trans-3-[(s)-1-{4-(4-methoxyphenylmethyl)-piperazine-1-yl carbonyl}-3-methylbutylcarbamoyl]oxirane-2-carboxylate was yielded as a white powder (yield: 97%) from ethyl trans-3-[(s)-1-{4-(4-methoxyphenylmethyl)-piperazine-1-yl carbonyl}-3-methylbutylcarbamoyl]oxirane-2-carboxylate (5.0 g) obtained above.

IR(KBr)cm⁻¹: 1630, 900.

| NMR(CD₃OD)δ: | |
|---|---|
| 0.94 | (6H, d, (CH₃)₂CH—) |
| 1.6 | (3H, m, —C<u>H</u>₂—C<u>H</u>—) |
| 2.46 | (4H, m, 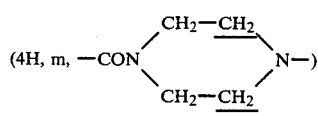) |
| 3.3-3.7 | (8H, m, 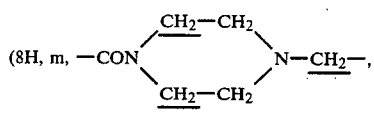, 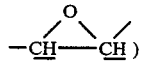) |
| 3.80 | (3H, s, —OC<u>H</u>₃) |
| 4.9 | (1H, m, —N—C<u>H</u>—CO—) |
| 6.94 | (2H, d, 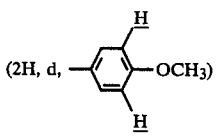) |
| 7.32 | (2H, d, 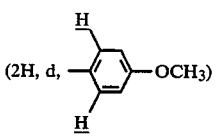) |

EXAMPLE 4

Under cooling with ice, a methylene chloride solution (30 ml) of N,N'-dicyclohexylcarbodiimide (41.2 g) was added dropwise to a methylene chloride solution (70 ml) containing tert-butoxycarbonyl-L-leucine monohydrate (4.98 g) and N-hydroxy succinimide (2.30 g), and the mixture was stirred at room temperature for 4 hours. While cooling again with ice, 1-(2,3,4-trimethoxyphenylmethyl)piperazine=dihydrochloride (6.79 g) was added, and triethylamine (8.5 ml) was then added dropwise. The mixture was stirred overnight at room temperature. After removal of methylene chloride by distillation under reduced pressure, ethyl acetate was added to the residue, and any insoluble matters were removed by filtration. The filtrate was washed first with an aqueous sodium bicarbonate solution and then with an aqueous saturated sodium chloride solution, dried over sodium sulfate and distilled under reduced pressure to remove the solvent, whereupon a crude reaction mixture was obtained as an oily viscous substance. This substance was purified by silica gel column chromatography (developing solvent:-chloroform:methanol=20:1) to yield 9.5 g of tert-butyl (s)-3-methyl-1-[4-(2,3,4-trimethoxyphenylmethyl)-piperazine-1-yl carbonyl]butylcarbamate as a colorless oily viscous substance (yield: 99%).

| NMR(CDCl₃)δ: | |
|---|---|
| 0.92 | (6H, m, (C<u>H</u>₃)₂CH—) |
| 1.13-1.84 | (12H, m, (C<u>H</u>₃)₃C—, —C<u>H</u>₂—C<u>H</u>—) |
| 2.30-2.60 | (4H, m, 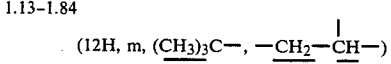) |
| 3.24-3.68 | (6H, m, 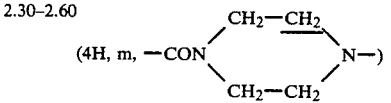) |
| 3.84 | (9H, m, Ar—OC<u>H</u>₃ × 3) |
| 4.56 | (1H, m, —N—C<u>H</u>—CO—) |
| 5.24 | (1H, m, —CON<u>H</u>—) |
| 6.56 | (1H, d, J=8Hz, aromatic proton) |
| 6.90 | (1H, d, J=8Hz, aromatic proton) |

While cooling with ice, hydrogen chloride gas was fed and saturated into ethyl acetate (200 ml) to which was then added an ethyl acetate solution (50 ml) of tert-butyl (s)-3-methyl-1-[4-(2,3,4-trimethoxyphenylmethyl)piperazine-1-yl carbonyl]butylcarbamate (9.5 g) obtained above. The mixture was stirred at room temperature for 2 hours. Ethyl acetate and excess hydrogen chloride were removed by distillation under reduced pressure to yield 8.6 g of 1-L-leucyl-4-(2,3,4-trimethoxyphenylmethyl)piperazine=dihydrochloride as a light yellow crystal (yield: 95%).

A small amount of the product was treated with two equivalents of triethylamine to obtain the corresponding free base which was found to be 1-L-leucyl-4-(2,3,4-trimethoxyphenylmethyl)piperazine by NMR.

| NMR(CDCl₃)δ: | |
|---|---|
| 0.93 | (6H, d, J=7.5Hz, (C<u>H</u>₃)₂CH—) |

NMR(CDCl$_3$)δ:

1.35 (2H, m, —C$\underline{H_2}$—CH—)

1.90 (1H, m, —CH$_2$—C$\underline{H}$—)

2.43 (4H, m, —CON⟨CH$_2$—CH$_2$⟩N—)
     (with piperazine ring CH$_2$—CH$_2$)

3.3–3.7 (6H, m, —CON⟨CH$_2$—CH$_2$⟩NC$\underline{H_2}$—)
     (with piperazine ring CH$_2$—CH$_2$)

3.84 (9H, s, Ar—OC$\underline{H_3}$ × 3)

3.93–4.23 (3H, m, N$\underline{H_2}$—C$\underline{H}$—)

6.57 (1H, d, J=9Hz, aromatic proton)
6.93 (1H, d, J=9Hz, aromatic proton)

Under cooling with ice, a methylene chloride solution (10 ml) of N,N'-dicyclohexylcarbodiimide (1.60 g) was added dropwise to a methylene chloride solution (20 ml) containing monoethyl trans-epoxy succinate (1.24 g) and N-hydroxy succinimide (0.89 g), and the mixture was stirred at room temperature for 4 hours. While cooling again with ice, 1-L-leucyl-4-(2,3,4-trimethoxyphenylmethyl)piperazine=dihydrochloride (3.52 g) was added, and triethylamine (4.4 ml) was then introduced. The mixture was stirred overnight at room temperature. After removal of methylene chloride by distillation under reduced pressure, ethyl acetate was added, and any insoluble matters were removed by filtration. The filtrate was washed first with an aqueous sodium bicarbonate solution and then with an aqueous saturated sodium chloride solution, dried over sodium sulfate and distilled under reduced pressure to remove the solvent, whereupon 4 g of a crude reaction mixture was obtained as an orange oily viscous substance. This substance was purified by silica gel column chromatography (developing solvent:chloroform:methanol=50:1) to yield 3.05 g of ethyl trans-3-[(s)-3-methyl-1-{4-(2,3,4-trimethoxyphenylmethyl)piperazine-1-yl carbonyl}butylcarbamoyl]oxirane-2-carboxylate as a colorless oily viscous substance (yield: 75.3%).

IR(KBr)cm$^{-1}$: 1755, 1685, 1630, 900.

NMR(CDCl$_3$)δ:

0.93 (6H, m, (C$\underline{H_3}$)$_2$CH—)

1.1–1.7 (6H, m, —C$\underline{H_2}$—C$\underline{H}$—, —CO$_2$CH$_2$CH$_3$)

2.40 (4H, m, —CON⟨CH$_2$—CH$_2$⟩N—)

3.3–3.7 (8H, m, —CON⟨CH$_2$—CH$_2$⟩N—C$\underline{H_2}$—)

(—C$\underline{H}$—O—C$\underline{H}$—)

3.8 (9H, s, Ar—OC$\underline{H_3}$ × 3)

4.16 (2H, d, J=7.5Hz, —CO$_2$C$\underline{H_2}$—)

4.84 (1H, m, —NH—C$\underline{H}$—CO—)

6.35–7.0 (3H, m, —N$\underline{H}$CO—, aromatic protons)

MS (m/e): 522(M$^+$+1), 181(100%).

Under cooling with ice, a 0.48N sodium hydroxide-ethanol solution (9.48 ml) was added to an ethanol solution (20 ml) of ethyl trans-3-[(s)-3-methyl-1-{4-(2,3,4-trimethoxyphenylmethyl)piperazine-1-yl carbonyl}butylcarbamoyl]-oxirane-2-carboxylate (2.38 g) obtained above, and the mixture was stirred at room temperature for 2.5 hours. After removal of ethanol by distillation under reduced pressure, water was added, and any insoluble matters were removed by filtration using sellaite. The filtrate was concentrated and dried under reduced pressure to yield 2.31 g of sodium trans-3-[(s)-3-methyl-1-{4-(2,3,4-trimethoxyphenylmethyl)-piperazine-1-yl carbonyl}butylcarbamoyl]oxirane-2-carboxylate as a light yellow powder (yield: 98%).

IR(KBr)cm$^{-1}$: 1620, 1390, 900.

NMR(CD$_3$OD)δ:

0.92 (6H, d, J=7Hz, (C$\underline{H_3}$)$_2$CH—)

1.3–1.7 (3H, m, —C$\underline{H_2}$—C$\underline{H}$—)

2.4 (4H, m, —CON⟨CH$_2$—CH$_2$⟩N—)

3.2–3.6 (8H, m, —CON⟨CH$_2$—CH$_2$⟩N—C$\underline{H_2}$—)

(—C$\underline{H}$—O—C$\underline{H}$—)

3.74 (9H, m, Ar—OC$\underline{H_3}$ × 3)

4.8 (1H, m, —N—C$\underline{H}$—CO—)

6.60 (1H, d, J=8Hz, aromatic proton)
6.88 (1H, d, J=8Hz, aromatic proton)

| -continued |
|---|
| NMR(CD$_3$OD)δ: |
| 8.04* (1H, m, —N<u>H</u>CO—) (* in DMSO-D$^6$) |

The thus obtained sodium salt was added to an equivalent of 0.1N hydrochloric acid and concentrated until the volume was reduced to a half. The solution was left to stand still, and the white crystal which had precipitated was collected by filtration, washed first with cold water and then with ethanol and dried under reduced pressure to yield the corresponding free acid.
mp: 190°–192° C. (decomposed).
IR(KBr)cm$^{-1}$: 1650, 900.

| NMR(DMSO-d$_6$)δ: |
|---|
| 0.84 (6H, d, (C<u>H</u>$_3$)$_2$CH—) |
| 1.3–1.7 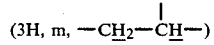 (3H, m, —C<u>H</u>$_2$—C<u>H</u>—) |
| 2.4 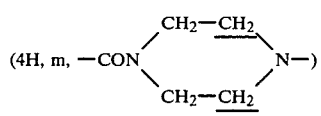 (4H, m, —CON< CH$_2$-CH$_2$ / CH$_2$-C<u>H$_2$</u> >N—) |
| 3.3–3.7 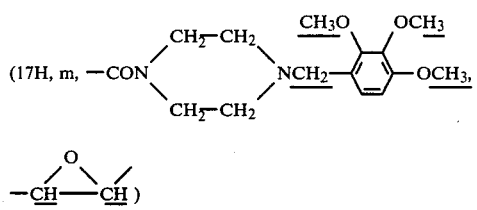 (17H, m, —CON< CH$_2$-CH$_2$ / CH$_2$-CH$_2$ >NC<u>H$_2$</u>—(aryl with CH$_3$O, OCH$_3$, OC<u>H$_3$</u>), —C<u>H</u>—O—C<u>H</u>—) |
| 4.6 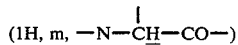 (1H, m, —N—C<u>H</u>—CO—) |
| 6.3 (1H, br, —CO$_2$<u>H</u> or N$^+$<u>H</u>—) |
| 6.48 (1H, d, J=8Hz, aromatic proton) |
| 6.72 (1H, d, J=8Hz, aromatic proton) |
| 8.3 (1H, br, —N<u>H</u>—) |

Elemental analysis as C$_{24}$H$_{35}$N$_3$O$_8$: Calculated (%); C: 58.41, H: 7.15, N: 8.51. Measured (%): C: 58.37, H: 7.23, N: 8.40.

Example 5

Tert-butoxycarbonyl-L-leucine monohydrate (7.47 g) and 1-ethylpiperazine (3.42 g) were condensed in the same manner as employed in the preparation of tert-butyl (s)-1-(4-diphenylmethylpiperazine-1-yl carbonyl)-3-methylbutylcarbamate to yield 6.4 g of tert-butyl (s)-1-(4-ethylpiperazine-1-yl carbonyl)-3-methylbutylcarbamate as a colorless viscous liquid (yield: 65%).

| NMR(CDCl$_3$)δ: |
|---|
| 0.88 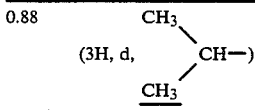 (3H, d, CH$_3$\CH—/CH$_3$) |
| 0.94 (3H, d, C<u>H$_3$</u>\CH—/CH$_3$) 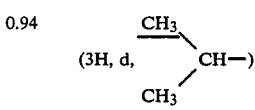 |

| -continued |
|---|
| NMR(CDCl$_3$)δ: |
| 1.04 (3H, t, J=7Hz, \NCH$_2$C<u>H$_3$</u>/) |
| 1.38 (9H, s, (C<u>H$_3$</u>)$_3$C—) |
| 1.3–1.8 (3H, m, —C<u>H$_2$</u>—C<u>H</u>—) |
| 2.30 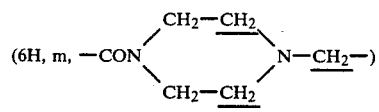 (6H, m, —CON< CH$_2$-CH$_2$ / CH$_2$-C<u>H$_2$</u> >N—C<u>H$_2$</u>—) |
| 3.40 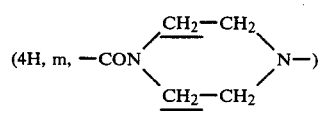 (4H, m, —CON< CH$_2$-CH$_2$ / CH$_2$-CH$_2$ >N—) |
| 4.40 (1H, m, —NH—C<u>H</u>—CO—) |
| 5.10 (1H, br, —N<u>H</u>—) |

In the same manner as employed in the preparation of 4-diphenylmethyl-1-L-leucylpiperazine=dihydrochloride, 6.0 g of 4-ethyl-1-L-leucylpiperazine=dihydrochloride was yielded as a white crystal (yield: quantitative) from tert-butyl (s)-1-(4-ethylpiperazine-1-yl carbonyl)-3-methylbutylcarbamate (6.4 g) obtained above.

Monoethyl trans-epoxy succinate (3.13 g) and 4-ethyl-1-L-leucylpiperazine=dihydrochloride (6.0 g) obtained above were condensed in the same manner as employed in the preparation of ethyl trans-3-[(s)-1-(4-diphenylmethylpiperazine-1-yl carbonyl)-3-methylbutylcarbamoyl]oxirane-2-carboxylate to yield 5.9 g of ethyl trans-3-[(s)-1-(4-ethylpiperazine-1-yl carbonyl)-3-methylbutylcarbamoyl]oxirane-2-carboxylate as a light yellow amorphous substance (yield: 82%).
IR(KBr)cm$^{-1}$: 1750, 1630, 890.

| NMR(CDCl$_3$)δ: |
|---|
| 0.96 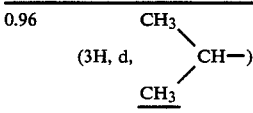 (3H, d, CH$_3$\CH—/CH$_3$) |
| 1.02 (3H, d, C<u>H$_3$</u>\CH—/CH$_3$) 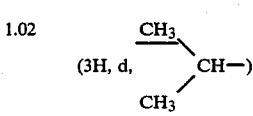 |
| 1.12 (3H, t, J=8Hz, —NCH$_2$C<u>H$_3$</u>) |
| 1.34 (3H, t, J=7Hz, —CO$_2$CH$_2$C<u>H$_3$</u>) |
| 1.4–1.8 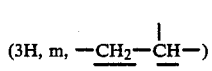 (3H, m, —C<u>H$_2$</u>—C<u>H</u>—) |

| NMR(CDCl₃)δ: | |
|---|---|
| 2.52 | (6H, m, 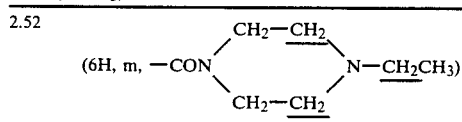) |
| 3.7 | (6H, m, 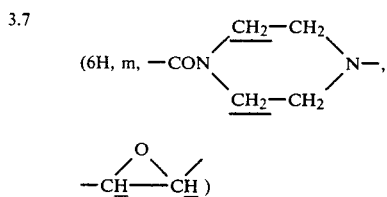) |
| | 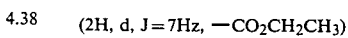 |
| 4.38 | (2H, d, J=7Hz, —CO₂C$\underline{H}$₂CH₃) |
| 5.12 | (1H, m, 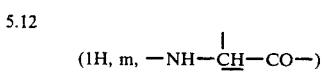) |
| 7.14, 7.40 | (1H, m, br, 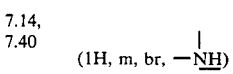) |

MS (m/e): 369(M⁺), 228, 113, 84(100%).

In the same manner as employed in the preparation of sodium trans-3-[(s)-1-(4-diphenylmethylpiperazine-1-yl carbonyl)-3-methylbutyl carbamoyl]oxirane-2-carboxylate, 5.1 g of sodium trans-3-[(s)-1-(4-ethylpiperazine-1-yl carbonyl)-3-methylbutylcarbamoyl]oxirane-2-carboxylate was yielded as a white powder (yield: 88%) from ethyl trans-3-[(s)-1-(4-ethylpiperazine-1-yl carbonyl)-3-methylbutylcarbamoyl]-oxirane-2-carboxylate (5.9 g) obtained above.

IR(KBr)cm⁻¹: 1620, 900.

| NMR(CD₃OD)δ: | |
|---|---|
| 0.96 | (6H, d, (C$\underline{H}$₃)₂CH—) |
| 1.12 | (3H, t, J=8Hz, NCH₂C$\underline{H}$₃) |
| 1.6 | (3H, m, 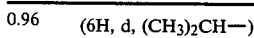) |
| 2.5 | (6H, m, 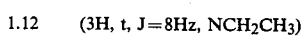) |
| 3.3-3.7 | (6H, m, 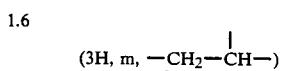) |
| 4.9 | (1H, m, 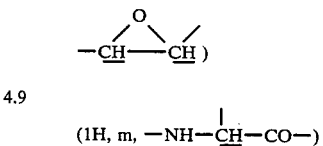) |

Example 6

Tert-butoxycarbonyl-L-leucine monohydrate (7.47 g) and 1-cinnamylpiperazine (6.06 g) were condensed in the same manner as employed in the preparation of tert-butyl (s)-1-(4-diphenylmethylpiperazine-1-yl carbonyl)-3-methylbutylcarbamate to yield 10.7 g of tert-butyl (s)-1-(4-cinnamylpiperazine-1-yl carbonyl)-3-methylbutylcarbamate as a colorless amorphous substance (yield: 86%).

| NMR(CDCl₃)δ: | |
|---|---|
| 0.88 | (3H, d, 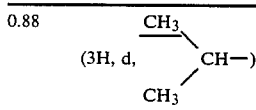) |
| 0.96 | (3H, d, 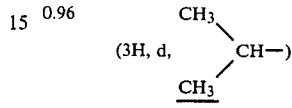) |
| 1.42 | (9H, s, (C$\underline{H}$₃)₃C—) |
| 1.3-1.9 | (3H, m, 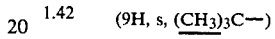) |
| 2.44 | (4H, m, 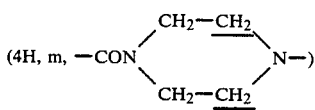) |
| 3.08 | (2H, d, J=7Hz, 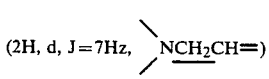) |
| 3.54 | (4H, m, 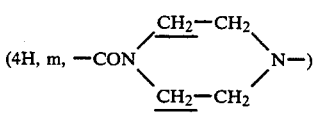) |
| 4.54 | (1H, m, 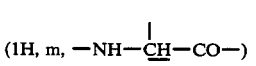) |
| 5.28 | (1H, br, 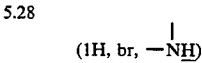) |
| 6.10 | (1H, dt, J=16Hz, 7Hz, —CH₂C$\underline{H}$=CH—) |
| 6.42 | (1H, d, J=16Hz, —CH=C$\underline{H}$—Ar) |
| 7.2 | (5H, m, aromatic proton) |

In the same manner as employed in the preparation of 4-diphenylmethyl-1-L-leucylpiperazine=dihydrochloride, 10.0 g of 4-cinnamyl-1-L-leucylpiperazine-dihydrochloride was yielded as a light yellow crystal (yield: quantitative) from tert-butyl (s)-1-(4-cinnamylpiperazine-1-yl carbonyl)-3-methylbutylcarbamate (10.7 g) obtained above.

4-Cinnamy-1-L-leucylpiperazine=dihydrochloride (10.0 g) obtained above and monoethyl trans-epoxy succinate (4.13 g) were condensed in the same manner as employed in the preparation of ethyl trans-3-[(s)-1-(4-diphenylmethylpiperazine-1-yl carbonyl)-3-methylbutylcarbamoyl]oxirane-2-carboxylate to yield 8.1 g of ethyl trans-3-[(s)-1-(4-cinnamylpiperazine-1-yl carbonyl)-3-methylbutylcarbamoyl]oxirane-2-carboxylate as a light yellow amorphous substance (yield: 69%).

IR(KBr)cm$^{-1}$: 1750, 1630.

NMR(CDCl$_3$)δ:

| | |
|---|---|
| 0.90 | (3H, d, CH$_3$–CH–CH$_3$) |
| 0.96 | (3H, d, CH$_3$–CH–CH$_3$) |
| 1.26 | (3H, t, J=7Hz, —CO$_2$CH$_2$C<u>H</u>$_3$) |
| 1.3–1.7 | (3H, m, —C<u>H</u>$_2$—C<u>H</u>—) |
| 2.44 | (4H, m, —CON(CH$_2$—CH$_2$)$_2$N—) |
| 3.10 | (2H, d, J=7Hz, —N—C<u>H</u>$_2$—CH=) |
| 3.4–3.6 | (6H, m, —CON(CH$_2$—CH$_2$)$_2$N—, —C<u>H</u>—C<u>H</u>(O)) |
| 4.16 | (2H, q, J=7Hz, —CO$_2$C<u>H</u>$_2$CH$_3$) |
| 4.88 | (1H, m, —NH—C<u>H</u>—CO—) |
| 6.10 | (1H, dt, J=16Hz, 7Hz, —CH$_2$—C<u>H</u>=CH—) |
| 6.44 | (1H, d, J=16Hz, —CH=C<u>H</u>—Ar) |
| 6.86 | (1H, d, —N<u>H</u>) |
| 7.1–7.3 | (5H, m, aromatic protons) |

In a manner similar to Example 1, 7.6 g of sodium trans-3-[(s)-(4-cinnamylpiperazine-1-yl carbonyl)-3-methylbutylcarbamoyl]oxirane-2-carboxylate was yielded as a light yellow powder (yield: 96%) from ethyl trans-3-[(s)-1-(4-cinnamylpiperazine-1-yl carbonyl)-3-methylbutylcarbamoyl]oxirane-2-carboxylate (8.0 g) obtained above.

IR(KBr)cm$^{-1}$: 1620, 890.

NMR(CD$_3$OD)δ:

| | |
|---|---|
| 0.94 | (6H, d, (C<u>H</u>$_3$)$_2$CH—) |
| 1.4–1.7 | (3H, m, —C<u>H</u>$_2$—C<u>H</u>—) |
| 2.48 | (4H, m, —CON(CH$_2$—CH$_2$)$_2$N—) |
| 3.12 | (2H, d, J=7Hz, —NC<u>H</u>$_2$CH=) |
| 3.2–3.6 | (6H, m, —CON(CH$_2$—CH$_2$)$_2$N—, —C<u>H</u>—C<u>H</u>(O)) |
| 4.8 | (1H, m, —NH—C<u>H</u>—CO—) |
| 6.12 | (1H, dt, J=16Hz, 7Hz, —CH$_2$—C<u>H</u>=CH—) |
| 6.48 | (1H, d, J=16Hz, —CH=C<u>H</u>—Ar) |
| 7.1–7.3 | (5H, m, aromatic protons) |

Example 7

Under cooling with ice, an ethyl acetate solution (40 ml) of N,N'-dicyclohexylcarbodiimide (10.3 g) was added dropwise to an ethyl acetate solution (150 ml) containing tert-butoxycarbonyl-L-leucine monohydrate (12.5 g) and N-hydroxy succinimide (5.76 g), and the mixture was stirred at room temperature for 3 hours. While cooling again with ice, 1-(2-pyridyl)piperazine (8.16 g) was added, and the mixture was stirred overnight at room temperature. The precipitate was removed by filtration, and the filtrate was washed first with an aqueous sodium carbonate solution and then with a saturated sodium chloride solution, dried over sodium sulfate and distilled under reduced pressure to remove the solvent, whereupon a crude reaction mixture was obtained. The reaction mixture was purified by silica gel column chromatography (developing solvent-:methylene chloride:methanol=10:1) to yield 16.1 g of tert-butyl (s)-3-methyl-1-[4-(2-pyridyl)piperazine-1-yl carbonyl]butylcarbamate (yield: 85.6%).

IR(neat)cm$^{-1}$: 1710, 1640, 1600, 775, 730.

NMR(CDCl$_3$)δ:

| | |
|---|---|
| 0.96 | (6H, m, (C<u>H</u>$_2$)$_2$CH—) |
| 1.46 | (9H, s, (C<u>H</u>$_3$)$_3$C—) |
| 1.4–1.8 | (3H, m, —C<u>H</u>$_2$—C<u>H</u>—) |
| 3.64 | (8H, m, —CON(CH$_2$—CH$_2$)$_2$N—) |
| 4.65 | (1H, m, —NH—C<u>H</u>—CO—) |

| NMR(CDCl$_3$)δ: | |
|---|---|
| 5.28 | (1H, br, —N<u>H</u>CO—) |
| 6.62–8.08 | (4H, m, aromatic protons) |

Under cooling with ice, hydrogen chloride gas was fed and saturated into ethyl acetate (200 ml), and tert-butyl (s)-3-methyl-1-[4-(2-pyridyl)piperazine-1-yl carbonyl]-butylcarbamate (16.0 g) obtained above was added gradually. The mixture was stirred for 30 minutes. The solvent and hydrogen chloride was removed by distillation under reduced pressure, and 200 ml of water was added to the white powder thus obtained to dissolve the powder therein. After washing with ethyl acetate, an aqueous sodium bicarbonate solution was added to bring the pH to 8. Followed by the addition of sodium chloride, extraction with 100 ml of ethyl acetate was repeated three times. After drying over sodium sulfate, the solvent was removed by distillation under reduced pressure to yield 9.16 g of 1-L-leucyl-4-(2-pyridyl)piperazine (yield: 78.0%).

IR(neat)cm$^{-1}$: 3350, 2950, 1635, 770, 725.

| NMR(CDCl$_3$)δ: | |
|---|---|
| 0.96 | (6H, m, (CH$_3$)$_2$CH—) |
| 1.4 | (3H, m, —CH$_2$—C<u>H</u>—) |
| 2.7 | (2H, br, —N<u>H</u>$_2$) |
| 3.64 | (9H, m, —CON⟨CH$_2$—CH$_2$⟩N—, —NH—C<u>H</u>—CO—) |
| 6.68–8.20 | (4H, m, aromatic protons) |

Under cooling with ice, an ethyl acetate solution (10 ml) of N,N'-dicyclohexylcarbodiimide (3.90 g) was added dropwise to an ethyl acetate solution (75 ml) containing monoethyl trans-epoxy succinate (3.03 g) and N-hydroxy succinimide (2.18 g), and the mixture was stirred overnight at room temperature. While cooling again with ice, an ethyl acetate solution (10 ml) of 1-L-leucyl-4-(2-pyridyl)piperazine (5.22 g) obtained above was added and stirred overnight at room temperature. The precipitate was removed by filtration, and the filtrate was washed first with an aqueous sodium bicarbonate solution and then with an aqueous saturated sodium chloride solution, dried over sodium sulfate and distilled under reduced pressure to remove the solvent, whereupon a crude reaction mixture was obtained. The reaction mixture was purified by silica gel column chromatography (developing solvent: ethyl acetate) to yield 7.01 g of ethyl trans-3-[(s)-3-methyl-1-{4-(2-pyridyl)piperazine-1-yl carbonyl}butylcarbamoyl]oxirane-2-carboxylate as a light yellow solid substance (yield: 92%).

IR(KBr)cm$^{-1}$: 1740, 1640, 900, 770.

| NMR(CDCl$_3$)δ: | |
|---|---|
| 0.96 | (6H, m, (CH$_3$)$_2$CH—) |
| 1.34 | (3H, t, J = 7Hz, —CO$_2$CH$_2$C<u>H</u>$_3$) |
| 1.6 | (3H, m, —C<u>H</u>$_2$—C<u>H</u>—) |
| 3.56–3.74 | (10H, m, —CON⟨CH$_2$—CH$_2$⟩N—, —C<u>H</u>—C<u>H</u> (epoxide)) |
| 4.24 | (2H, m, —COC<u>H</u>$_2$—) |
| 5.08 | (1H, m, —NH—C<u>H</u>—CO—) |
| 6.68, 7.18, 7.62 and 8.30 | (5H, m, —N<u>H</u>CO—, aromatic protons) |

In the same manner as employed for the preparation of sodium trans-3-[(s)-1-(4-diphenylmethylpiperazine-1-yl carbonyl)-3-methylbutylcarbamoyl]oxirane-2-carboxylate, 6.8 g of trans-3-[(s)-1-{4-(2-pyridyl)piperazine-1-yl carbonyl}-3-methylbutylcarbamoyl]oxirane-2-carboxylate was yielded as a light yellow powder (yield: quantitative) from ethyl trans-3-[(s)-1{4-(2-pyridyl)piperazine-1-yl carbonyl}-3-methylbutylcarbamoyl]-oxirane-2-carboxylate (6.70 g) obtained above.

IR(KBr)cm$^{-1}$: 1660–1590, 900, 770.

| NMR(DMSO-d$_6$)δ: | |
|---|---|
| 0.90 | (6H, m, (CH$_3$)$_2$CH—) |
| 1.44 | (3H, m, —C<u>H</u>$_2$—C<u>H</u>—) |
| 2.98, 3.28 and 3.46 | (10H, m, —CON⟨CH$_2$—CH$_2$⟩N—, —C<u>H</u>—C<u>H</u> (epoxide)) |
| 4.65 | (1H, m, —NH—C<u>H</u>—CO—) |
| 6.6, 7.36, 7.9 and 8.1 | (5H, m, —N<u>H</u>CO—, aromatic protons) |

Example 8

Tert-butoxycarbonyl-L-leucine monohydrate (12.5 g) and 1-(2-pyrimidinyl)piperazine (8.21 g) were condensed in the same manner as employed in the preparation of tertbutyl (s)-3-methyl-1-[4-(2-pyridyl)piperazine- 1-yl-carbonyl]-butylcarbamate to yield 13.4 g of tert-butyl (s)-3-methyl-1-[4-(2-pyrimidinyl)piperazine-1-yl carbonyl]butylcarbamate (yield: 71%).

IR(KBr)cm$^{-1}$: 1710, 1630, 1590, 800.

| NMR(CDCl$_3$)δ: | |
|---|---|
| 1.00 | (6H, m, (CH$_3$)$_2$CH—) |
| 1.5 | (9H, s, (CH$_3$)$_3$C—) |
| 1.4–1.8 | (3H, m, —CH$_2$—CH—) |
| 4.0 | (8H, m, —CON(CH$_2$CH$_2$)$_2$N—) |
| 4.84–5.47 | (2H, br, —CONH—, —NH—CH—CO—) |
| 6.8, 8.68 | (3H, m, aromatic protons) |

In the same manner as employed for the preparation of 1-L-leucyl-4-(2-pyridyl)piperazine, 9.76 g of 1-L-leucyl-4-(2-pyrimidinyl)piperazine was yielded (yield: quantitative) from tert-butyl (s)-3-methyl-1-[4-(2-pyrimidinyl)piperazine-1-yl carbonyl]butylcarbamate (13.3 g) obtained above.

IR(KBr)cm$^{-1}$: 2960–2940, 1630, 1590, 800.

| NMR(CDCl$_3$)δ: | |
|---|---|
| 0.99 | (6H, m, (CH$_3$)$_2$CH—) |
| 1.4 | (3H, m, —CH$_2$—CH—) |
| 1.70 | (2H, m, NH$_2$—) |
| 3.92 | (9H, m, —CON(CH$_2$CH$_2$)$_2$N—, —NH—CH—CO—) |
| 6.75, 8.59 | (3H, m, aromatic protons) |

Monoethyl trans-epoxy succinate (3.52 g) and 1-L-leucyl-4-(2-pyrimidinyl)piperazine (6.10 g) were condensed in the same manner as employed in the preparation of ethyl trans-3-[(s)-3-methyl-1-{4-(2-pyridyl)piperazine-1-yl carbonyl}butylcarbamoyl]oxirane-2-carboxylate to yield 8.50 g of ethyl trans-3-[(s)-3-methyl-1-{4-(2-pyrimidinyl)piperazine-1-yl carbonyl}butylcarbamoyl]oxirane-2-carboxylate (yield: 92.1%).

IR(KBr)cm$^{-1}$: 1745, 1630, 1583, 900, 800.

| NMR(CDCl$_3$)δ: | |
|---|---|
| 0.98 | (6H, m, (CH$_3$)$_2$CH—) |
| 1.36 | (3H, t, J = 7Hz, —CO$_2$CH$_2$CH$_3$) |
| 1.6 | (3H, m, —CH$_2$—CH—) |
| 3.8 | (10H, m, —N(CH$_2$CH$_2$)$_2$N—, —CH—CH< (oxirane)) |
| 4.36 | (2H, m, —CO$_2$CH$_2$—CH$_3$) |
| 5.12 | (1H, m, —NH—CH—CO—) |
| 6.70, 8.52 | (3H, m, aromatic protons) |
| 7.18 | (1H, m, —NH—CO—) |

In the same manner as employed in the preparation of sodium trans-3-[(s)-3-methyl-1-{4-(2-pyridyl)piperazine-1-yl carbonyl}butyl-carbamoyl]oxirane-2-carboxylate, 7.60 g of sodium trans-3-[(s)-3-methyl-1-{4-(2-pyrimidinyl)piperazine-1-yl carbonyl}butylcarbamoyl]oxirane-2-carboxylate was yielded as a light yellow powder (yield: quantitative) from ethyl trans-3-[(s)-3-methyl-1-{4-(2-pyrimidinyl)piperazine-1-yl carbonyl}butylcarbamoyl]oxirane-2-carboxylate (8.00 g) obtained above.

IR(KBr)cm$^{-1}$: 1680–1600, 1580, 900, 800.

| NMR(DMSO-d$_6$)δ: | |
|---|---|
| 0.96 | (6H, m, (CH$_3$)$_2$CH—) |
| 1.6 | (3H, m, —CH$_2$—CH—) |
| 3.20, 3.50, 3.66 | (10H, m, —CON(CH$_2$CH$_2$)$_2$N—, —CH—CH< (oxirane)) |
| 5.0 | (1H, m, —NH—CH—CO—) |
| 6.90, 8.72 | (4H, m, aromatic protons, —NHCO—) |

The thus obtained sodium salt (518 mg) was neutralized by the addition of an equivalent of 0.1N hydrochloric acid and then extracted with ethyl acetate. The extracted solution was dried over magnesium sulfate, and the solvent was removed by distillation to yield the corresponding free acid as a white crystal [mp: 83.5° to 86° C. (decomposed)] (yield: 449 mg, 92%).

IR(KBr)cm$^{-1}$: 1740, 1630, 1590, 900, 800.

| NMR(CDCl$_3$)δ: | |
|---|---|
| 0.96 | (6H, m, (C$\underline{H_3}$)$_2$CH—) |
| 1.54 | (3H, m, —C$\underline{H_2}$C$\underline{H}$—) |
| 3.68 | (10H, m, —N$\diagup\overset{CH_2-CH_2}{\diagdown}$N—, $\diagup\overset{O}{\diagdown}$ —C$\underline{H}$——C$\underline{H}$—) |
| 4.96 | (1H, m, —NHC$\underline{H}$CO—) |
| 6.46, 8.10 | (3H, m, aromatic protons) |
| 7.24 | (1H, m, —N$\underline{H}$CO—) |
| 9.90 | (1H, br, —CO$_2\underline{H}$) |

MS (m/e): 391(M+), 347, 122, 86(100%).
Elemental analysis as C$_{18}$H$_{25}$N$_5$O$_5$: Calculated (%): C:55.23, H:6.44, N:17.89. Measured (%): C:55.01, H:6.51, N:17.62.

Example 9

Under stirring and cooling with ice, an ethanol solution (100 ml) of potassium hydroxide was added dropwise to an ethanol solution (100 ml) of diethyl (2R,3R)-epoxy succinate (18.8 g). The solution was stirred overnight and cooled with ice. The precipitate was filtered, washed with cold ethanol and ether and dried under reduced pressure to yield 16.0 g of potassium monoethyl (2R,3R)-epoxy succinate (yield: 81%).

[α]D=−86.4° (C=1, H$_2$O)

Potassium monoethyl (2R,3R)-epoxy succinate (15.0 g) was dissolved in an aqueous saturated sodium chloride solution (75 ml) under stirring and cooling with ice, and concentrated hydrochloric acid (7.6 ml) was added. The solution was extracted with ethyl acetate (100 ml), washed with an aqueous saturated sodium chloride solution, and filtered through a glass filter with magnesium sulfate placed thereon, and fed to a reaction vessel in which N-hydroxy succinimide (8.7 g) had been previously placed. Under stirring and cooling with ice, and an ethyl acetate solution (60 ml) of N,N'-dicyclohexylcarbodiimide (15.6 g) was added dropwise at a temperature of at most 15° C., and the mixture was stirred at room temperature for 2 hours. Thereafter, an ethyl acetate solution (28.7 g) of 1-L-leucyl-4-(2,3,4-trimethoxyphenylmethyl)piperazine (28.7 g) was added dropwise, and the mixture was stirred overnight at room temperature. The reaction solution was again cooled with ice, and the precipitate was removed by filtration. The filtrate was washed with an aqueous sodium bicarbonate solution and an aqueous saturated sodium chloride solution, dried over magnesium sulfate and then distilled under reduced pressure to remove the solvent, whereupon a yellow oily viscous substance was obtained. This substance was purified by silica gel column chromatography (developing solvent: chloroform:methanol=50:1) to yield 29.6 g of ethyl (2R,3R)-3-[(s)-3-methyl-1-{4-(2,3,4-trimethoxyphenylmethyl)-pipera- zine-1-yl carbonyl}butylcarbamoyl]oxirane-2-carboxylate as a colorless oily viscous substance (yield: 75%).

IR(KBr)cm$^{-1}$: 1755, 1685, 1630, 900.

| NMR(CDCl$_3$)δ: | |
|---|---|
| 0.93 | (6H, m, (C$\underline{H_3}$)$_2$CH—) |
| 1.15–1.76 | (6H, m, —C$\underline{H_2}$—C$\underline{H}$—, —CO$_2$CH$_2$C$\underline{H_3}$) |
| 2.39 | (4H, m, —CON$\diagup\overset{CH_2CH_2}{\diagdown}$N—) |
| 3.20–3.70 | (8H, m, —CON$\diagup\overset{CH_2CH_2}{\diagdown}$NC$\underline{H_2}$—, $\diagup\overset{O}{\diagdown}$ —C$\underline{H}$——C$\underline{H}$—) |
| 3.76 | (9H, m, C$\underline{H_3}$O, OC$\underline{H_3}$, OC$\underline{H_3}$ on aromatic ring) |
| 4.10 | (2H, q, J = 7.5Hz, —CO$_2$C$\underline{H_2}$—) |
| 4.76 | (1H, m, —NHC$\underline{H}$CO—) |
| 6.40 | (1H, d, J = 8Hz, aromatic proton) |
| 6.73 | (1H, d, J = 8Hz, aromatic proton) |
| 6.84 | (1H, d, J = 7Hz, —N$\underline{H}$CO—) |

[α]D=−51.9° (C=1.0, ethanol).

1N sulfuric acid (26.8 ml) was added to an ether solution (50 ml) of ethyl (2R,3R)-3-[(s)-3-methyl-1-{4-(2,3,4-trimethoxyphenylmethyl)piperazine-1-yl carbonyl} butylcarbamoyl]-oxirane-2-carboxylate (14.0 g), and the mixture was stirred. Subsequently, the aqueous layer was collected by separation and distilled under reduced pressure to yield 15.0 g of ethyl (2R,3R)-[(s)-3-methyl-1-{4-(2,3,4-trimethoxyphenylmethyl)-piperazine-1-yl}carbonyl butylcarbamoyl]oxirane-2-carboxylate ½ sulfate as a colorless crystal (yield: 98%).

IR(KBr)cm$^{-1}$: 1745, 1645, 895.

| NMR(DMSO-d$_6$ + D$_2$O)δ: | |
|---|---|
| 0.90 | (6H, m, (C$\underline{H_3}$)$_2$CH—) |
| 1.22 | (3H, t, J = 7Hz, —CO$_2$CH$_2$C$\underline{H_3}$) |
| 1.3–1.75 | (3H, m, —C$\underline{H_2}$C$\underline{H}$—) |
| 2.6–3.0 | (4H, m, —CON$\diagup\overset{CH_2CH_2}{\diagdown}$N—) |

-continued

| NMR(DMSO-d$_6$ + D$_2$O)δ: | |
|---|---|
| 3.2–3.9 | (17H, m, —CON⟨CH$_2$CH$_2$⟩$_2$NC$\underline{H_2}$—), 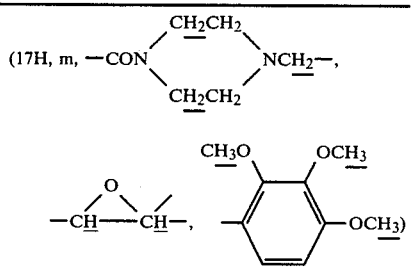 |
| 4.07 | (2H, q, J = 7Hz, —CO$_2$C$\underline{H_2}$—) |
| 4.62 | (1H, m, —NHC$\underline{H}$CO—) |
| 6.62 | (1H, d, J = 8Hz, aromatic proton) |
| 6.92 | (1H, d, J = 8Hz, aromatic proton) |
| 8.52 | (1H, d, J = 7Hz, —N$\underline{H}$CO—) |

[α]D = −42.0° (C=1.0, 1N H$_2$SO$_4$).

Under cooling with ice, a 0.48N sodium hydroxide-ethanol solution (55.6 ml) was added to an ethanol solution (100 ml) of ethyl (2R,3R)-3-[(s)-3-methyl-1-{4-(2,3,4-trimethoxyphenylmethyl)piperazine-1-yl carbonyl}butylcarbamoyl]oxirane-3-carboxylate (14.0 g), and the mixture was stirred at room temperature for 2.5 hours. Ethanol was removed by distillation under reduced pressure, and water was added. Any insoluble matters were removed by filtration, and the filtrate was concentrated and dried under reduced pressure to yield 13.5 g of sodium (2R,3R)-3-[(s)-3-methyl-1-{4-(2,3,4-trimethoxyphenylmethyl)piperazine-1-yl carbonyl}butylcarbamoyl]oxirane-2-carboxylate as a light yellow powder (yield: 98%).

IR(KBr)cm$^{-1}$: 1620, 900.

| NMR(DMSO-d$_6$)δ: | |
|---|---|
| 0.90 | (6H, m, (C$\underline{H_3}$)$_2$CH—) |
| 1.30–1.70 | (3H, m, —C$\underline{H_2}$C$\underline{H}$—) |
| 2.35 | (4H, m, —CON⟨CH$_2$CH$_2$⟩$_2$N—) 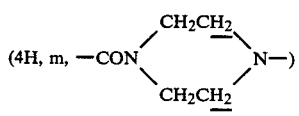 |
| 3.00–3.70 | (8H, m, —CON⟨C$\underline{H_2}$C$\underline{H_2}$⟩$_2$N—C$\underline{H_2}$—), 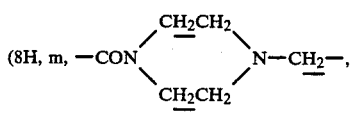 —C$\underline{H}$——C$\underline{H}$—) |
| 3.76 | (9H, m, 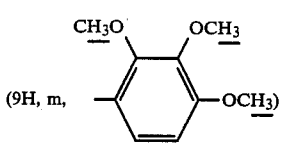) |

| NMR(DMSO-d$_6$)δ: | |
|---|---|
| 4.70 | (1H, m, —NHC$\underline{H}$—CO—) |
| 6.64 | (1H, d, J = 8Hz, aromatic proton) |
| 6.88 | (1H, d, J = 8Hz, aromatic proton) |
| 8.08 | (1H, d, —N$\underline{H}$CO—) |

[α]D = −43.8° (C=1, H$_2$O).

An acetone solution (2 ml) of oxalic acid dihydrate (0.25 g) was added to an acetone solution (6 ml) of ethyl (2R,3R)-3-[(s)-3-methyl-1-{4-(2,3,4-trimethoxyphenyl-methyl)-piperazine-1-yl carbonyl}butylcarbamoyl]oxirane-2-carboxylate (1.04 g), and the crystal which had precipitated was collected by filtration and dried to yield 0.99 g of ethyl (2R,3R)-3-[(s)-3-methyl-1-{4-(2,3,4-trimethoxyphenylmethyl)piperazine-1-yl carbonyl} butylcarbamoyl]oxirane-2-carboxylate oxalate as a colorless crystal (yield: 81%).

mp: 132°–133° (decomposed).

IR(KBr)cm$^{-1}$: 1750, 1640, 900.

| NMR(DMSO-d$_6$ + D$_2$O)δ: | |
|---|---|
| 0.87 | (6H, m, (C$\underline{H_3}$)$_2$CH—) |
| 1.22 | (3H, t, J = 7Hz, —CO$_2$CH$_2$C$\underline{H_3}$) |
| 1.30–1.70 | (3H, m, —C$\underline{H_2}$C$\underline{H}$—) |
| 2.50–2.90 | (4H, m, —CON⟨CH$_2$CH$_2$⟩$_2$N—) 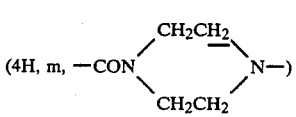 |
| 3.30–3.90 | (17H, m, —CON⟨CH$_2$CH$_2$⟩$_2$NC$\underline{H_2}$—, 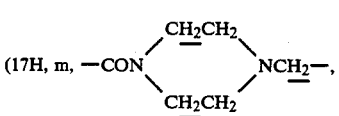 —C$\underline{H}$——C$\underline{H}$—, 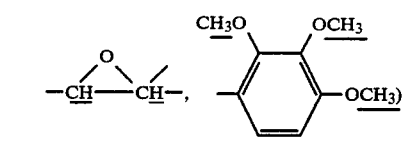) |
| 4.16 | (2H, q, J = 7Hz, —CO$_2$C$\underline{H_2}$CH$_3$) |
| 4.72 | (1H, m, —NHC$\underline{H}$CO—) |
| 6.76 | (1H, d, J = 8Hz, aromatic proton) |
| 7.05 | (1H, d, J = 8Hz, aromatic proton) |
| 8.72 | (1H, d, J = 8Hz, —N$\underline{H}$CHCO—) |

[α]D = −37.6° (C=0.99, H$_2$O).

Elemental analysis as C$_{28}$H$_{41}$N$_3$O$_{12}$: Calculated (%): C:54.98, H:6.76, N:6.87. Measured (%): C:54.80, H:6.87, N:6.89.

Example 10

Under stirring and cooling with ice, an ethanol solution (35 ml) of potassium hydroxide (1.82 g) was added dropwise to an ethanol solution (35 ml) of diethyl (2S,3S)-epoxy succinate (6.09 g). The mixture was stirred overnight and cooled. The precipitate was collected by filtration, washed with cold ethanol and ether and then dried to yield 4.55 g of a potassium salt of monoethyl (2S,3S)-epoxy succinate (yield: 71%).

$[\alpha]_D^{23} = +83.2°$ (C=1, H$_2$O).

The potassium salt of monoethyl (2S,3S)-epoxy succinate (4.22 g) was dissolved in an aqueous saturated sodium chloride solution (21 ml) under stirring and cooling with ice to which was then added concentrated hydrochloric acid (2.14 ml). The mixture was extracted with ethyl acetate (28 ml), washed with an aqueous saturated sodium chloride solution, filtered through a glass filter with magnesium sulfate placed thereon, and fed to a reaction vessel in which N-hydroxy succinimide (2.45 g) had been previously placed. Under cooling with ice and stirring, an ethyl acetate solution (17 ml) of N,N'-dicyclohexylcarbodiimide (4.39 g) was added dropwise at a temperature of at most 15° C. and stirred at room temperature for 2 hours. Thereafter, an ethyl acetate solution (17 ml) of 1-L-leucyl-4-(2,3,4-trimethoxyphenylmethyl)piperazine (8.07 g) was added dropwise, and the mixture was stirred overnight at room temperature. The reaction solution was again cooled with ice, and the precipitate was removed by filtration. The filtrate was washed with an aqueous sodium bicarbonate solution and a saturated sodium chloride solution, dried over magnesium sulfate and then distilled under reduced pressure to remove the solvent, whereupon a yellow oily viscous substance was obtained. This substance was purified by silica gel column chromatography (developing solvent: chloroform:methanol=50:1) to yield 7.40 g of ethyl (2S,3S)-[3-methyl-1-{4-(2,3,4-trimethoxyphenylmethyl)piperazine-1-yl carbonyl}butylcarbamoyl]oxirane-2-carboxylate as a colorless oily viscous substance (yield: 67%).

IR(KBr)cm$^{-1}$: 1755, 1685, 1630, 900.

NMR(DMSO-d$_6$)δ:

| 0.90 | (6H, m, (CH$_3$)$_2$CH—) |
|---|---|
| 1.08–1.80 | (6H, m, —CH$_2$CH—, —CO$_2$CH$_2$CH$_3$) |
| 2.38 | (4H, m, —CON(CH$_2$CH$_2$)$_2$N—) |
| 3.20–4.00 | (17H, m, —CON(CH$_2$CH$_2$)$_2$NCH$_2$—, —CH(O)CH—, trimethoxyphenyl (CH$_3$O, OCH$_3$, OCH$_3$)) |
| 4.22 | (2H, q, J = 7.5Hz, —CO$_2$CH$_2$—) |
| 4.84 | (1H, m, —NHCHCO—) |
| 6.78 | (1H, d, J = 8Hz, aromatic proton) |
| 7.03 | (1H, d, J = 8Hz, aromatic proton) |
| 8.72 | (1H, d, J = 8Hz, —NHCO—) |

$[\alpha]_D^{23} = +48.2°$ (C=1.0, ethanol).

1N sulfuric acid (6.13 ml) was added to an ether solution (11 ml) of ethyl (2S,3S)-3-[(s)-3-methyl-1-{4-(2,3,4-trimethoxyphenylmethyl)piperazine-1-yl carbonyl}-butylcarbamoyl]oxirane-2-carboxylate (3.20 g) obtained above, and the mixture was stirred. Thereafter, the aqueous layer was collected by separation and distilled under reduced pressure to yield 3.32 g of a ½ sulfate of ethyl (2S,3S)-3-[(s)-3-methyl-1-{4-(2,3,4-trimethoxyphenylmethyl)piperazine-1-yl carbonyl}butylcarbamoyl]oxirane-2-carboxylate as a white powder (yield: 95%).

IR(KBr)cm$^{-1}$: 1745, 1645, 895.

NMR(DSMO-d$_6$ + D$_2$O)δ:

| 0.88 | (6H, m, (CH$_3$)$_2$CH—) |
|---|---|
| 1.24 | (3H, t, J = 7Hz, —CO$_2$CH$_2$CH$_3$) |
| 1.3–1.75 | (3H, m, —CH$_2$CH—) |
| 2.6–3.0 | (4H, m, —CON(CH$_2$CH$_2$)$_2$N—) |
| 3.2–3.9 | (17H, m, —CON(CH$_2$CH$_2$)$_2$NCH$_2$, —CH(O)CH—, trimethoxyphenyl (CH$_3$O, OCH$_3$, OCH$_3$)) |
| 4.24 | (2H, q, J = 7Hz, —CO$_2$CH$_2$—) |
| 4.84 | (1H, m, —NHCHCO—) |
| 6.92 | (1H, d, J = 9Hz, aromatic proton) |
| 7.22 | (1H, d, J = 9Hz, aromatic proton) |
| 8.84 | (1H, d, J = 8Hz, —NHCO—) |

$[\alpha]_D = +47.3°$ (C=1.0, H$_2$O).

Under cooling with ice, a 0.47N sodium hydroxide-ethanol solution (4.15 ml) was added to an ethanol solution (7.5 ml) of ethyl (2S,3S)-3-[(s)-3-methyl-1-{4-(2,3,4-trimethoxyphenylmethyl)piperazine-1-yl carbonyl}butylcarbamoyl]-oxirane-2-carboxylate (1.04 g), and the mixture was stirred at room temperature for 2.5 hours. After removal of ethanol by distillation under reduced pressure, water was added, and any insoluble matters were removed by filtration. The filtrate was concentrated and dried under reduced pressure to yield 1.00 g of sodium (2S,3S)-3-[(s)-3-methyl-1-{4-(2,3,4-trimethoxyphenylmethyl)piperazine-1-yl carbonyl}butylcarbamoyl]-oxirane-2-carboxylate as a light yellow powder (yield: 97%).

IR(KBr)cm$^{-1}$: 1625, 895.

NMR(DMSO-d$_6$)δ:

0.86    (6H, m, (C<u>H</u>$_3$)$_2$CH—) 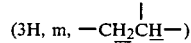

1.20–1.70

(3H, m, —C<u>H</u>$_2$C<u>H</u>—)

2.34

(4H, m, —CON\<CH$_2$CH$_2$\>N—) 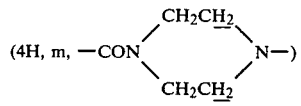

3.00–3.60

(8H, m, —CON\<CH$_2$CH$_2$\>N—CH$_2$—, —C<u>H</u>—C<u>H</u>—) 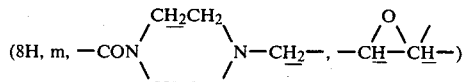

3.70–3.85

(9H, m, CH$_3$O, OCH$_3$, OCH$_3$ phenyl) 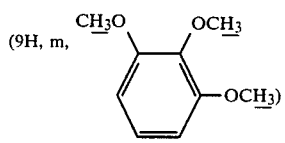

4.75

(1H, m, —NHC<u>H</u>—CO—) 

6.72    (1H, d, J = 8Hz, aromatic proton)
6.96    (1H, d, J = 8Hz, aromatic proton)
8.12    (1H, d, —N<u>H</u>CO—)

[α]$_D$ = +29.3° (C=0.99, H$_2$O).

An acetone solution (2 ml) of oxalic acid dihydrate (0.25 g) was added to an acetone solution (6 ml) of ethyl (2S,3S)-3-[(s)-3-methyl-1-{4-(2,3,4-trimethoxyphenylmethyl)-piperazine-1-yl carbonyl}butylcarbamoyl]oxirane-2-carboxylate (1.04 g), and the crystal which had precipitated was collected by filtration and dried to yield 1.03 g of an oxalate of ethyl (2S,3S)-3-[(s)-3-methyl-1-{4-(2,3,4-trimethoxyphenylmethyl)piperazine-1-yl carbonyl}butylcarbamoyl]oxirane-2-carboxylate as a colorless crystal (yield: 84%).

mp: 132.5°–133.5° C. (decomposed).
IR: 1755, 1640, 900.

NMR(DMSO-d$_6$ + D$_2$O)δ:

0.88    (6H, m, (C<u>H</u>$_3$)$_2$CH—) 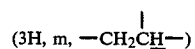

1.24    (3H, t, J = 7Hz, —CO$_2$CH$_2$C<u>H</u>$_3$)
1.30–1.70

(3H, m, —C<u>H</u>$_2$C<u>H</u>—)

2.50–2.90

(4H, m, —CON\<CH$_2$CH$_2$\>N—) 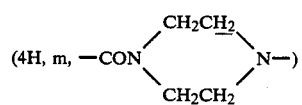

3.30–3.90

(17H, m, —CON\<CH$_2$CH$_2$\>NCH$_2$—, ...) 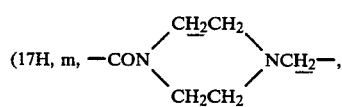

-continued (—C<u>H</u>—C<u>H</u>—, CH$_3$O, OCH$_3$, OCH$_3$) 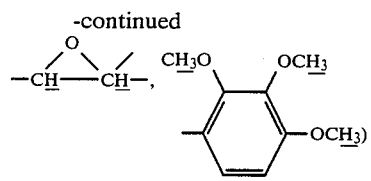

4.20    (2H, q, J = 7Hz, —CO$_2$C<u>H</u>$_2$CH$_3$)
4.80

(1H, m, —NHC<u>H</u>CO—) 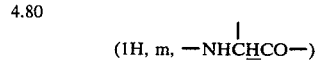

6.81    (1H, d, J = 8Hz, aromatic proton)
7.10    (1H, d, J = 8Hz, aromatic proton)

8.72

(1H, d, J = 8Hz, —N<u>H</u>CHCO—) 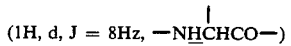

[α]$_D^{15}$ = +46.2° (C = 1.01, H$_2$O)

Elemental analysis as C$_{28}$H$_{41}$N$_3$O$_{12}$: Calculated (%): C:54.98 H:6.76 N:6.87. Measured (%): C:54.87 H:6.69 N:6.76.

Example 11

A monoisobutyl ester of epoxy succinic acid (6.5 g) was dissolved in ethyl acetate (40 ml) to which was added N-hydroxy succinimide (4.0 g). While stirring the mixture under cooling with ice, an ethyl acetate solution (25 ml) of N,N'-dicyclohexylcarbodiimide (7.5 g) was added dropwise at a temperature of at most 15° C. and stirred at room temperature for 2 hours. An ethyl acetate solution (25 ml) of 1-L-leucyl-4-(2,3,4-trimethoxyphenylmethyl)piperazine (13.1 g) was then added dropwise and stirred overnight at room temperature. The reaction solution was again cooled with ice, and the precipitate was removed by filtration. The filtrate was washed with an aqueous sodium bicarbonate solution and an aqueous saturated sodium chloride solution, dried over magnesium sulfate and distilled under reduced pressure to remove the solvent, whereupon a yellow oily viscous substance was obtained. This substance was purified by silica gel column chromatography (developing solvent: chloroform:methanol=50:1) to yield 10.5 g of isobutyl trans-[(s)-3-methyl-1-{4-(2,3,4-trimethoxyphenylmethyl)piperazine-1-yl carbonyl}butylcarbamoyl]oxirane-2-carboxylate as a light yellow oily viscous substance (yield: 55%).

NMR(CDCl$_3$)δ:

0.84–1.04    (12H, m, —CH$_3$ × 4)
1.36–2.16    (4H, m, (CH$_3$)$_2$C<u>H</u>—CH$_2$—, (CH$_3$)$_2$CH—C<u>H</u>$_2$—O—)

2.40–2.64

(4H, m, —CON\<CH$_2$CH$_2$\>N—) 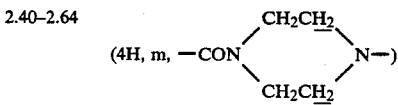

3.40–3.80

(8H, m, —CON\<CH$_2$CH$_2$\>N—CH$_2$—, ...) 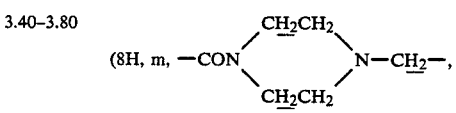

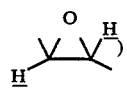

| | | |
|---|---|---|
| 3.88–4.12 | (11H, m, 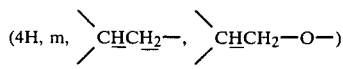, —OC$\underline{H}_3$, —CO$_2$C$\underline{H}_2$—) |
| 5.04 | (1H, m, —HN—C$\underline{H}$—CO—) 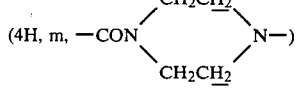 |
| 6.76 | (1H, d, J = 9Hz, aromatic proton) |
| 6.96 | (1H, m, —N$\underline{H}$CO—) |
| 7.12 | (1H, d, J = 9Hz, aromatic proton) |

In the same manner as in Example 9, the product was converted to a sulfate to yield a white powder.

IR(KBr)cm$^{-1}$: 1750, 1645, 900.

NMR(DMSO-d$_6$ + D$_2$O)δ:

| | |
|---|---|
| 0.90 | (12H, m, —C$\underline{H}_3$ × 4) |
| 1.32–2.10 | (4H, m, >C$\underline{H}$CH$_2$—, >C$\underline{H}$CH$_2$—O—) |
| 2.64–2.96 | (4H, m, —CON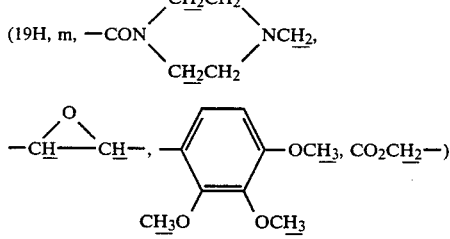N—) |
| 3.40–4.00 | (19H, m, —CON<...>NCH$_2$, —C$\underline{H}$—C$\underline{H}$—, , OC$\underline{H}_3$, CO$_2$C$\underline{H}_2$—) |
| 4.76 | (1H, m, —HNC$\underline{H}$CO—) |
| 6.81 | (1H, d, J = 9Hz, aromatic proton) |
| 7.12 | (1H, d, J = 9Hz, aromatic proton) |
| 8.76 | (1H, m, —CON$\underline{H}$—) |

Example 12

In a manner similar to Example 9, ethyl (2R,3R)-3-[(s)-3-methyl-1-{4-(2-pyrimidinyl)piperazine-1-yl carbonyl}-butylcarbamoyl]oxirane-2-carboxylate was yielded from monoethyl (2R,3R)-epoxysuccinate and 1-L-leucyl-4-(2-pyrimidinyl)-piperazine.

IR(KBr)cm$^{-1}$: 1745, 1630, 1583, 900, 800.

NMR(CDCl$_3$)δ:

| | |
|---|---|
| 0.84–1.04 | (6H, m, (C$\underline{H}_3$)$_2$CH—) |
| 1.28 | (3H, t, J = 7Hz, —CO$_2$CH$_2$C$\underline{H}_3$) |
| 1.36–1.72 | (3H, m, —C$\underline{H}_2$C$\underline{H}$—) |
| 3.40–3.96 | (10H, m, —N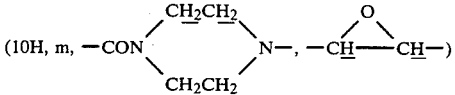N—, —C$\underline{H}$—C$\underline{H}$—) |
| 4.19 | (2H, q, J = 7Hz, —CO$_2$C$\underline{H}_2$CH$_3$) |
| 4.94 | |
| | (1H, m, —NHC$\underline{H}$CO—) 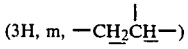 |
| 6.45 | (1H, m, aromatic proton) |
| 6.77 | (1H, d, J = 8Hz, —N$\underline{H}$CO—) |
| 8.20 | (2H, m, aromatic proton) |

[α]D = −52°(C = 1.0, CHCl$_3$)

In a manner similar to Example 9, ethyl (2R,3R)-3-[(s)-3-methyl-1-{4-(2-pyrimidinyl)piperazine-1-yl carbonyl}-butylcarbamoyl]oxirane-2-carboxylate was hydrolyzed with sodium hydroxide to yield sodium (2R,3R)-3-[(s)-3-methyl-1-{4-(2-pyrimidinyl)piperazine-1-yl carbonyl}butylcaramoyl]-oxirane-2-carboxylate.

IR(KBr)cm$^{-1}$: 1680–1600, 1590, 900.

NMR(DMSO-d$_6$):

| | |
|---|---|
| 0.90 | (6H, m, (C$\underline{H}_3$)$_2$CH—) |
| 1.51 | (3H, m, —C$\underline{H}_2$C$\underline{H}$—) 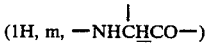 |
| 3.04–4.12 | (10H, m, —CON<...>N—, —C$\underline{H}$—C$\underline{H}$—) |
| 4.83 | (1H, m, —NHC$\underline{H}$CO—) 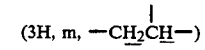 |
| 6.67 | (1H, m, aromatic proton) |
| 8.40 | (3H, m, aromatic proton, —N$\underline{H}$CO—) |

[α]D = −44° (C=1.0, H$_2$O).

Example 13

In a manner similar to Example 9, ethyl (2S,3S)-3-[(s)-3-methyl-1-{4-(2-pyrimidinyl)piperazine-1-yl carbonyl}-butylcarbamoyl]oxirane-2-carboxylate was yielded from monoethyl (2S,3S)-epoxy succinate and 1-L-leucyl-4-(2-pyrimidinyl)-piperazine.

IR(KBr)cm$^{-1}$: 1745, 1630, 1583, 900, 800.

NMR(CDCl$_3$)δ:

| | |
|---|---|
| 0.84–1.04 | (6H, m, (C$\underline{H}_3$)$_2$CH—) |
| 1.28 | (3H, t, J = 7Hz, —CO$_2$CH$_2$C$\underline{H}_3$) |
| 1.36–1.72 | (3H, m, —C$\underline{H}_2$C$\underline{H}$—) 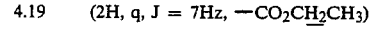 |
| 3.40–3.96 | (10H, m, —N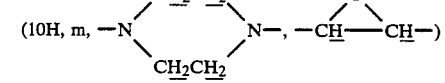N—, —C$\underline{H}$—C$\underline{H}$—) |
| 4.19 | (2H, q, J = 7Hz, —CO$_2$C$\underline{H}_2$CH$_3$) |
| 4.94 | (1H, m, —NHC$\underline{H}$CO—) 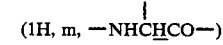 |

-continued 6.45 (1H, m, aromatic proton)
6.95 (1H, d, J = 8Hz, —NHCO—)
8.20 (2H, m, aromatic proton)

$[\alpha]D = +78$ (C=1.0, CHCl$_3$).

In a manner similar to Example 9, ethyl (2S,3S)-3-[(s)-3-methyl-1-{4-(2-pyrimidinyl)piperazine-1-yl carbonyl}-butylcarbamoyl]oxirane-2-carboxylate was hydrolyzed with sodium hydroxide to yield sodium (2S,3S)-3-[(s)-3-methyl-1-{4-(2-pyrimidinyl)piperazine-1-yl carbonyl}butylcarbamoyl]-oxirane-2-carboxylate.

IR(KBr)cm$^{-1}$: 1680–1600, 1580, 890.

NMR(DMSO-d$_6$):

0.91 (6H, m, (CH$_3$)$_2$CH—)

1.51 (3H, m, —CH$_2$CH—)

3.05–4.06 (10H, m, —CON⟨CH$_2$CH$_2$⟩N, —CH—CH—)
                     ⟨CH$_2$CH$_2$⟩      \O/

4.86 (1H, m, —NHCHCO—)

6.69 (1H, m, aromatic proton)
8.29 (1H, d, J = 8Hz, —NHCO—)
8.41 (2H, m, aromatic proton)

$[\alpha]D = +38°$ (C=1.0, H$_2$O).

Example 14

N-[trans-2,3-epoxy-3-ethoxycarbonylpropyonyl]-L-leucine [IR(KBr)cm$^{-1}$: 1730, 1650, 900, NMR(CDCl$_3$): 0.98 (6H, m, (CH$_3$)$_2$CH—), 1.32 (3H, t, J=7 Hz, CH$_3$CH$_2$O—), 1.68 (3H, m,

—CH$_2$CH—), 3.42–3.83 (2H, m,

—CHCH—),
 \O/

4.26 (2H, q, J=7 Hz, CH$_3$CH$_2$O—), 4.60 (1H, m,

—NHCHCO—), 6.74 (0.5H, d, J=8 Hz, —NHCO—), 6.91 (0.5H, d, J=8 Hz, —NHCO—), 9.76 (1H, s, —CO$_2$H)] (100 g) was dissolved in ethyl acetate (15 ml), and N-hydroxy succinimide (0.421 g) was added and sufficiently stirred. While cooling the solution, an ethyl acetate solution (5 ml) of N,N'-dicyclohexylcarbodiimide (0.754 g) was added dropwise. The mixture was stirred at room temperature for 3 hours and again cooled, and an ethyl acetate solution (4.5 ml) of trimetazidine (0.974 g) was added dropwise. The mixture was stirred overnight at room temperature. The mixture was again cooled, and any insoluble matters were removed by filtration. The filtrate was washed with an aqueous saturated sodium bicarbonate solution and a saturated sodium chloride solution, dried over sodium sulfate and then distilled to remove the solvent, whereby a light yellow oily substance was obtained. The substance was purified by silica gel column chromatography (developing solvent: chloroform:methanol=50:1) to yield 1.70 g of ethyl trans-3-[(s)-3-methyl-1-{4-(2,3,4-trimethoxyphenylmethyl)-piperazine-1-yl carbonyl}butylcarbamoyl]oxirane-2-carboxylate as a colorless oily viscous substance (yield: 89%).

Test Example 1

Effects against an experimental myocardial infarction

White male rabbits having a weight of about 2 kg were anesthetized with pentobarbital sodium (35 mg/kg, i.v.). The chest wall of each animal was incised under artificial respiration, and the anterior descending artery was ligated (about 7 mm downward of the starting portion). 24 Hours later, the heart was taken out, and a myocardium between the cadiac apex and the ligated portion was sliced to have a thickness of 2 mm and stained to distinguish the infarction-affected portions by a phosphorylase reaction, whereupon the area of the necrotic portion was calculated by planimetory. Medicinal substances were administered 5 minutes prior to the ligation (T/2 mg/kg, i.v.), continuously from immediately after the ligation to one hour later (T/4 mg/kg/hr, by constant dropping), 2 hours after the ligation (T/8 mg/kg, i.v.) and 3 hours after theligation (T/8 mg/kg, i.v.). Each medicinal substance was administered in the form of a physiological sodium chloride solution. Where the substance was hardly soluble, it was used in the form of a salt. To a control group was administered only a physiological sodium chloride solution. (T means a total amount of administration.)

The results obtained are shown in Table 1.

TABLE 1

| Compounds | Amounts administered T (mg/kg, i. v.) | Number of cases | Death rates (mean ± S.E. %) | Inhibition rates (%) |
|---|---|---|---|---|
| Control group having no medicinal substance administered | — | 20 | 14.9 ± 0.7 | — |
| 1 | 80 | 8 | 11.2 ± 0.5 | 24.8 |
| 2 | 200 | 8 | 11.9 ± 0.6 | 20.1 |
| 3 | 200 | 8 | 11.9 ± 0.8 | 20.1 |
| 4 | 200 | 8 | 10.5 ± 0.9 | 29.5 |
| 5 | 200 | 8 | 11.8 ± 0.9 | 20.8 |
| 6 | 100 | 8 | 11.1 ± 0.6 | 25.5 |
| 7 | 200 | 8 | 11.6 ± 0.7 | 22.1 |
| 8 | 200 | 8 | 11.1 ± 0.8 | 25.5 |
| Control group having no medicinal substance administered | — | 20 | 14.1 ± 1.0 | — |
| 9 | 40 | 8 | 11.5 ± 1.2 | 18.4 |
| 10 | 40 | 8 | 10.5 ± 1.1 | 25.5 |
| 11 | 40 | 8 | 10.0 ± 1.0 | 29.1 |
| 12 | 40 | 8 | 11.3 ± 1.2 | 19.9 |
| 13 | 200 | 8 | 9.8 ± 0.9 | 30.5 |
| 14 | 200 | 8 | 10.7 ± 0.9 | 24.1 |
| 15 | 200 | 8 | 11.1 ± 0.7 | 23.0 |
| 16 | 200 | 8 | 10.7 ± 0.4 | 26.0 |
| Control group having no medicinal substance administered | — | 20 | 14.6 ± 1.0 | — |

TABLE 1-continued

| Compounds | Amounts administered T (mg/kg, i. v.) | Number of cases | Death rates (mean ± S.E. %) | Inhibition rates (%) |
|---|---|---|---|---|
| Propranolol hydrochloride (INDERAL INJECTION- trademark) | 1 | 8 | 13.7 ± 1.1 | 6.2 |
| | 2 | 7 | 11.2 ± 1.0 | 23.3 |
| | 4 | 8 | 10.7 ± 1.1 | 26.7 |
| Verapanil hydrochloride (dissolved in a physiological sodium chloride solution) | 2 | 10 | 11.0 ± 1.3 | 24.7 |

Compounds:
1: Sodium trans-3-[(s)-1-(4-diphenylmethylpiperazine-1-yl carbonyl-3-methyl-butyl-carbamoyl]oxirane-2-carboxylate
2: Sodium trans-3-[(s)-1-(4-benzylpiperazine-1-yl carbonyl)-3-methylbutylcarbamoyl]oxirane-2-carboxylate
3: Sodium trans-3-[(s)-1-{4-(4-methoxyphenylmethyl)piperazine-1-yl carbonyl}-3-methylbutylcarbamoyl]oxirane-2-carboxylate
4: Sodium trans-3-[(s)-3-methyl-1-{4-(2,3,4-trimethoxy-phenylmethyl)piperazine-1-yl carbonyl}butylcarbamoyl]-oxirane-2-carboxylate
5: Sodium trans-3-[(s)-1-(4-ethylpiperazine-1-yl carbonyl)-3-methylbutylcarbamoyl]oxirane-2-carboxylate
6: Sodium trans-3-[(s)-1-(4-cinnamylpiperazine-1-yl carbonyl)-3-methylbutylcarbamoyl]oxirane-2-carboxylate
7: Sodium trans-3-[(s)-1-{4-(2-pyridyl)piperazine-1-yl carbonyl}-3-methylbutylcarbamoyl]oxirane-2-carboxylate
8: Sodium trans-3-[(s)-3-methyl-1-{4-(2-pyrimidinyl)piperazine-1-yl carbonyl}butylcarbamoyl]oxirane-2-carboxylate
9: Isobutyl trans-3-[(s)-3-methyl-1-{4-(2,3,4-trimethyloxy-phenylmethyl)piperazine-1-yl carbonyl}butylcarbamoyl]-oxirane-2-carboxylate ½ sulfate.
10: Ethyl trans-3-[(s)-3-methyl-1-{4-(2,3,4-trimethoxy-phenylmethyl)piperazine-1-yl carbonyl}butylcarbamoyl]-oxirane-2-carboxylate ½ sulfate
11: Ethyl (2R,3R)—3-[(s)-3-methyl-1-{4-(2,3,4-trimethoxy-phenylmethyl)piperazine-1-yl carbonyl}butylcarbamoyl]-oxirane-2-carboxylate ½ sulfate
12: Ethyl (2S,3S)—3-[(s)-3-methyl-1-{4-(2,3,4-trimethoxy-phenylmethyl)piperazine-1-yl carbonyl}butylcarbamoyl]-oxirane-2-carboxylate ½ sulfate
13: Sodium (2R,3R)—3-[(s)-3-methyl-1-{4-(2,3,4-trimethoxy-phenylmethyl)piperazine-1-yl carbonyl}butylcarbamoyl]-oxirane-2-carboxylate
14: Sodium (2S,3S)—3-[(s)-3-methyl-1-{4-(2,3,4-trimethoxy-phenylmethyl)piperazine-1-yl carbonyl}butylcarbamoyl]-oxirane-2-carboxylate
15: Sodium (2R,3R)—3-[(s)-3-methyl-1-{4-(2-pyrimidinyl)piperazine-1-yl carbonyl}butylcarbamoyl]oxirane-2-carboxylate
16: Sodium (2S,3S)—3-[(s)-3-methy-1-{4-(2-pyrimidinyl)piperazine-1-yl carbonyl}butylcarbamoyl]oxirane-2-carboxylate It will be seen that the control group to which no medicinal substance was administered exhibited a death rate of about 14.1 to 14.9%, while the administered group to which the medicinal substances of the present invention were applied exhibited a death rate of from 9.8 to 11.9%. Thus, it has been confirmed that the medicinal substances are significantly effective to suppress the death rate.

Test Example 2

Acute toxicity test ddN Type male mice having a weight of from 20 to 28 g were used. Medicinal substances were administered intravenously from the tails of the mice. The results obtained are shown in Table 2.

TABLE 2

| Compounds | LD50 mice (mg/kg i. v.) |
|---|---|
| Control group having no medicinal substance administered | — |
| 1 | 174 |
| 2 | MLD > 1125 |
| 3 | MLD > 1125 |
| 4 | MLD > 1125 |
| 5 | MLD > 1125 |
| 6 | MLD = 1000–1125 |
| 7 | MLD > 1125 |
| 8 | MLD > 1125 |

TABLE 2-continued

| Compounds | LD50 mice (mg/kg i. v.) |
|---|---|
| Control group having no medicinal substance administered | — |
| 9 | 440 |
| 10 | — |
| 11 | 374 |
| 12 | 345 |
| 13 | MLD > 1125 |
| 14 | MLD > 1125 |
| 15 | MLD > 1125 |
| 16 | MLD > 1125 |
| Control group having no medicinal substance administered | — |
| Propranolol hydrochloride (INDERAL INJECTION- trademark) | 28 |
| Verapanil hydrochloride (dissolved in a physiological sodium chloride solution) | 15 |

Compounds: Compounds 1 to 16 are the same as denoted in Table 1.

It will be seen that even when the medicinal substances of the invention were administered in an amount ranging up to 1 g/kg of the animal weight, no particular changes were observed in the test animals in most cases. Thus, it has been confirmed that the substances of the invention have a high level of safety.

Example 15

Medicinal formulation (tablets)

Film-coated tablets were prepared to have the following composition per tablet (220 mg).

| | |
|---|---|
| Sodium trans-3-[(s)-3-methyl 1-{4-(2-pyrimidinyl) piperazine-1-yl carbonyl}butylcarbamoyl]oxirane-2-carboxylate | 50 mg |
| Lactose | 100 mg |
| Crystal cellulose | 50 mg |
| Magnesium stearate | 1 mg |
| Hydroxypropylmethyl cellulose | 15 mg |
| Hydroxypropyl cellulose | 4 mg |

Other compounds of the invention which are useful as the active ingredient may be made in the form of film-coated tablets by the same formulation.

Example 16

Medicinal formulation (granules)

Granules were prepared to have the following composition per gram of the granules.

| | |
|---|---|
| Sodium trans-3-[(s)-1-(4-diphenylmethylpiperazine-1-yl carbonyl)-3-methylbutylcarbamoyl]oxirane-2-carboxylate | 200 mg |
| Lactose | 500 mg |
| Corn starch | 300 mg |

Other compounds of the invention which are useful as the active ingredient may be made in the form of granules by the same formulation.

EXAMPLE 17

Medicinal formulation (injections)

(a) Ampoules were prepared to have the following composition per ampoule.

| | |
|---|---:|
| Sodium trans-3-[(s)-3-methyl-1-{4-(2,3,4-trimethoxy-phenylmethyl)piperazine-1-yl carbonyl}butyl-carbamoyl]oxirane-2-carboxylate | 100 mg |
| Potassium hydrogenphosphate buffer solution (0.4 M solution) | 1 ml |

Sterilized distilled water was added to the above composition to bring the total amount to 10 ml.

(b) Ampoules were prepared to have the following composition per ampoule.

| | |
|---|---:|
| Ethyl (2R,3R)-3-[(s)-3-methyl-1-{4-(2,3,4-trimethoxy-phenylmethyl)piperazine-1-yl carbonyl}butylcarbamoyl]oxirane-2-carboxylate ½ sulfate | 20 mg |

Sterilized distilled water was added to the above composition to bring the total amount to 10 ml.

Other compounds of the invention which are useful as the active ingredient may be made in the form of injections by similar formulations.

Having now fully described this invention, it will be apparent to one of ordinary skill in the art that many and modifications can be made thereto without departing the spirit or scope of the invention as set forth herein.

What is claimed is:

1. A compound of the formula (1), $$\begin{array}{c} H \quad O \quad CONHCHCON \\ R^1O_2C \quad H \quad CH_2 \\ CH(CH_3)_2 \end{array} \begin{array}{c} CH_2-CH_2 \\ CH_2-CH_2 \end{array} N-R^2 \quad (1)$$

where $R^1$ is a hydrogen atom, or a straight or branched chain alkyl group having 1 to 4 carbon atoms, and $R^2$ is a straight or branched chain alkyl group having 1 to 4 carbon atoms, $$-CH_2-\underset{(OCH_3)_n}{\bigcirc} \quad , \quad -CH_2-CH=CH-\bigcirc \quad ,$$

$$-CH\underset{\bigcirc}{\overset{\bigcirc}{\diagup}} \quad , \quad -\underset{N}{\overset{N}{\diagup\!\!\!\bigcirc}} \quad \text{or} \quad -\underset{N}{\overset{N}{\diagup\!\!\!\bigcirc}} ,$$

in which n is an integer of 0 to 2, or a pharmaceutically acceptable salt thereof.

2. The compound as claimed in claim 1 and having a (2R,3R)-configured epoxy group.

3. The compound as claimed in claim 1 and having a (2S,3S)-configured epoxy group.

4. The compound of claim 1 being trans-3-[(s)-3-methyl-1-{4-(2-pyrimidinyl)piperazine-1-yl carbonyl}-butylcarbamoyl]oxirane-2-carboxylic acid.

5. The compound of claim 4 being (2S,3S)-3-[(s)-3-methyl-1-{4-(2-pyrimidinyl)piperazine-1-yl carbonyl}-butylcarbamoyl]oxirane-2-carboxylic acid.

6. A composition for preventing or treating myocardial infarction, comprising:

(a) a compound of the formula (1), $$\begin{array}{c} H \quad O \quad CONHCHCON \\ R^1O_2C \quad H \quad CH_2 \\ CH(CH_3)_2 \end{array} \begin{array}{c} CH_2-CH_2 \\ CH_2-CH_2 \end{array} N-R^2 \quad (1)$$

wherein
$R^1$ is a hydrogen atom, or a straight or branched $C_1$-$C_4$ alkyl group, and
$R^2$ is a straight or branched $C_1$-$C_4$ alkyl group, $$-CH_2-\underset{(OCH_3)_n}{\bigcirc} \quad , \quad -CH_2-CH=CH-\bigcirc ,$$

$$-CH\underset{\bigcirc}{\overset{\bigcirc}{\diagup}} \quad , \quad -\underset{N}{\overset{N}{\diagup\!\!\!\bigcirc}} \quad \text{or} \quad -\underset{N}{\overset{N}{\diagup\!\!\!\bigcirc}} ,$$

wherein n is 0 to 2 or a pharmaceutically acceptable salt thereof, in an amount effective to prevent or treat myocardial infarction, and (b) a pharmaceutically acceptable carrier.

7. The composition of claim 6, wherein the carrier is selected from the group consisting of
fillers,
binding agents,
disintegrators and
lubricants.

8. The composition of claim 7 in a form selected from the group consisting of
injections,
powders,
capsules,
granules,
tablets and
ampoules.

9. The composition of claim 8, wherein the tablets comprise:
a carrier selected from the group consisting of lactose, saccharose, sodium chloride, glucose solution, starch, calcium carbonate, crystal cellulose and silicic acid;
a binder selected from the group consisting of water, ethanol, propanol, glucose, a starch solution, a gelatin solution, carboxyl methyl cellulose, methyl cellulose and potassium phosphate;
a disintegrator selected from the group consisting of dried starch, sodium alginate, agar powder, sodium hydrogencarbonate, calcium carbonate, stearic acid monoglyceride, starch and lactose;

a lubricant selected from the group consisting of a stearate, boric acid powder and solid polyethylene glycol.

10. The composition of claim 8, wherein the carrier for the injections is selected from the group consisting of water, ethyl alcohol, propylene glycol, polyoxyethylene sorbit and a sorbitan ester.

11. The composition of claim 10, further comprising:
(a) a compound selected from the group consisting of sodium chloride, glucose and glycerine, in an amount sufficient to form an isotonic solution, and
(b) a dissolving assistant, a buffer, or a preserving agent.

* * * * *